United States Patent [19]
Carozzi et al.

[11] Patent Number: 6,069,301
[45] Date of Patent: May 30, 2000

[54] ANTIBODIES WHICH BIND TO INSECT GUT PROTEINS AND THEIR USE

[75] Inventors: Nadine Barbara Carozzi, Raleigh, N.C.; Michael Gene Koziel, Clive, Iowa

[73] Assignee: Novartis Finance Corporation, New York, N.Y.

[21] Appl. No.: 08/765,469

[22] PCT Filed: Jun. 20, 1995

[86] PCT No.: PCT/IB95/00497

§ 371 Date: Dec. 20, 1996

§ 102(e) Date: Dec. 20, 1996

[87] PCT Pub. No.: WO96/00783

PCT Pub. Date: Jan. 11, 1996

Related U.S. Application Data

[63] Continuation-in-part of application No. 08/267,641, Jun. 28, 1994, abandoned.

[51] Int. Cl.$^7$ .............................. A01H 5/00; A01H 5/10; C07H 21/04; C12N 1/21; C12N 5/14; C12N 15/74; C12N 15/82

[52] U.S. Cl. .................... 800/302; 435/243; 435/252.3; 435/320.1; 435/419; 530/391.7; 536/23.53; 800/279

[58] Field of Search ...................... 530/391.7; 536/23.53; 536/23.4; 424/152.1; 435/332, 419, 320.1, 243, 252.3, 468; 800/298, 302, 278, 279

[56] References Cited

U.S. PATENT DOCUMENTS

| | | | |
|---|---|---|---|
| 4,816,567 | 3/1989 | Cabilly et al. | 530/387.1 |
| 4,946,778 | 8/1990 | Ladner et al. | 435/69.6 |
| 5,196,320 | 3/1993 | Gillies | 435/697 |
| 5,290,914 | 3/1994 | Wilcox et al. | 530/350 |
| 5,306,628 | 4/1994 | Sivasubramanian et al. | 435/69.7 |
| 5,665,595 | 9/1997 | Petell et al. | 530/288.23 |

FOREIGN PATENT DOCUMENTS

| | | |
|---|---|---|
| 0526397A1 | 7/1992 | European Pat. Off. . |
| 0438312A2 | 1/1997 | European Pat. Off. . |
| WO91/06320 | 5/1991 | WIPO . |
| WO91/17254 | 11/1991 | WIPO . |

OTHER PUBLICATIONS

Azuma, et al., "Discrete Localization of Distinct Alkaline Phosphatase Isozymes in the Cell Surface of Silkworm Midgut Epithelium", *The Journal of Experimental Zoology*, 251:108–112 (1989).

Batra, J.K., et al., "single–Chain Immunotoxins Directed at the Human Transferrin Receptor Containing *Pseudomonas* Exotoxim A or Diptheria Toxin: Anti–TFR (Fv)–PE40 and DT388–Anti–TFR(Fv)", *Molecular and Cellular Biology*, 11(4):2200–2205 (1991).

Brinkmann, U. et al., "B3(Fv)–PE38KDEL, a Single–chain Immunotoxin That Causes Complete Regression of a Human Carcinoma in Mice", *PNAS*, 88:8616–8620 (1991).

Chaudhary, V.K., et al., "A Recombinant Immunotoxin Consisting of Two Antibody Variable Domains Fused to Pseudomonas Exotoxin", *Nature*, 339:394–397 (1989).

Chaudhary, V.K., et al., "A Recombinant Single–chain Immunotoxin Composed of Anti–Tac Variable Regions and a Truncated Diphtheria Toxin", *PNAS*, 87:9491–9494 (1990).

Crankshaw et al., "Interspecies Cross–Reactivity of an Antibody to Southern Armyworm (*Spodoptera eridana*) Midgut Nadph–Cytochrome C Reductase", *Insect Biochem.*, 11(5):593–597 (1981).

Federici, B.A., Insecticidal Bacterial Proteins Identify the Midgut Epithelium as a Source of Novel Target Sites for Insect Control, *Archives of Insect Biochemistry and Physiology*, 22:357–371 (1993).

Gräf, et al., "Cloning and sequencing of cDNA encoding the putative insect plasma membrane V–ATPase Subunit A", *FEBS Lett*, 300(2):119–122 (1992).

Gutierrez et al., Antibodies From Chagas Patients Serum Bind to the Gut Epithelial Cell Surface of *Triatoma infestants*, *Micr. Electr. Biol. Cel.*, 15(2):145–158 (1991).

Hiatt et al., "Monoclonal antibody engineering in plants", *FEBS*, 307(1):71–75 (1992).

Oddou, P., et al., "Identification and characterization of *Heliothis virescens* midgut membrane proteins binding *Bacillus thuringiensis* δ–endotoxins", *Eur. J. Biochem.*, 202:673–680 (1991).

Oddou, P., et al., "Immunologically unrelated *Heliothis* sp. and *Spodoptera* sp. midgut membrane–proteins bind *Bacillus thuringiensis* CryIA(b) δ–endotoxin", *Eur. J. Biochem.*, 212:145–150 (1993).

Pastan, I. et al., "Recombinant Toxins as Novel Therapeutic Agents", *Annu. Rev. Biochem.*, 61:331–354 (1992).

Ryerse et al., "Peritrophic Membrane Structure and Formation in the Larva of a Moth, *Heliothis*", *Tissue and Cell*, 24(5):751–771 (1992).

Schots et al., "'Plantibodies': a flexible approach to design resistance against pathogens", *Neth. J. Pl. Path.*, 98(2):183–191 (1992).

Tavladoraki, et al., "Transgenic plants expressing a functional single–chain Fv antibody are specifically protected from virus attach", *Nature*, 366:469–472 (1993).

*Primary Examiner*—Lynette R. F. Smith
*Assistant Examiner*—Amy J. Nelson
*Attorney, Agent, or Firm*—J. Timothy Meigs; Gary M. Pace

[57] ABSTRACT

Antibodies, monoclonal antibodies or fragments thereof which bind to brush border membrane vesicles of insect gut and the gene or genes which encode these proteins are provided. The monoclonal antibodies bind the gut of a target insect but do not bind to mammalian brush border membranes or to plant microsomes. The antibodies and the genes encoding them find use in constructing hybrid toxins for control of insect pests.

**27 Cla

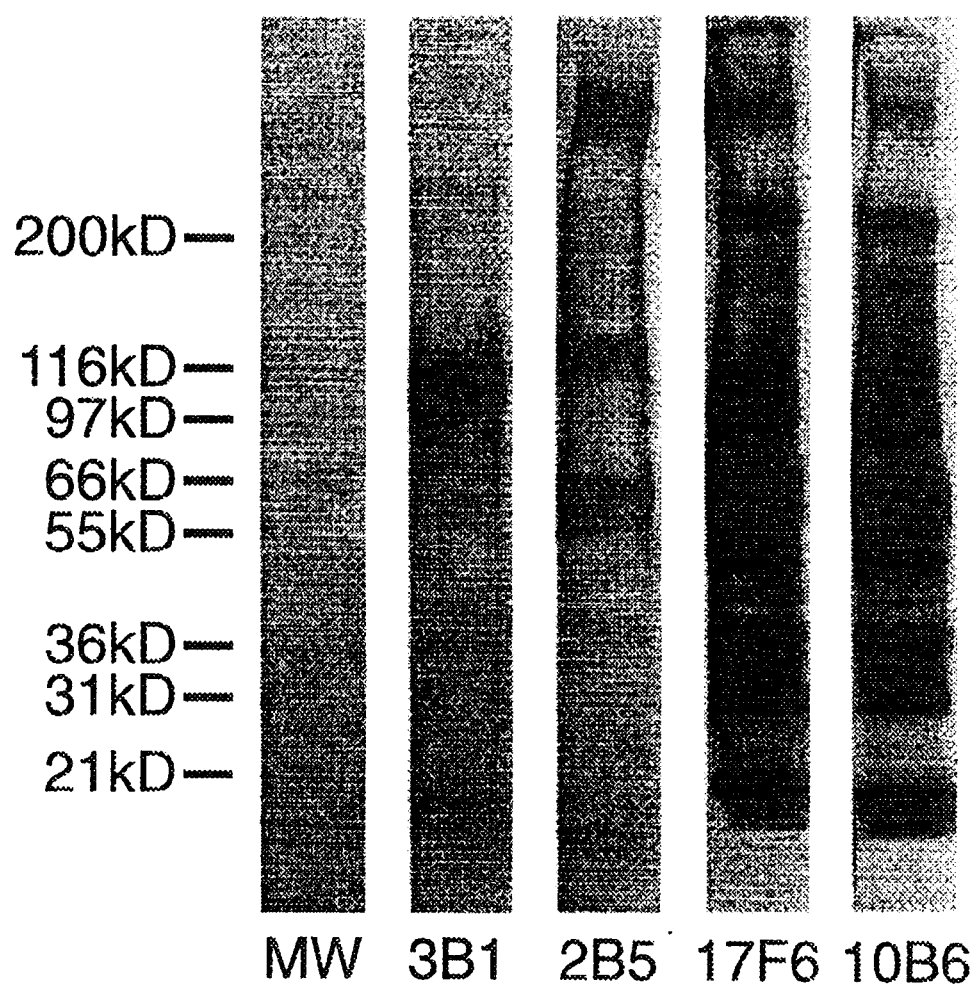

ANTIBODIES WHICH BIND TO INSECT GUT PROTEINS AND THEIR USE

This application is a 371 of PCT/IB95/00497, filed Jun. 20, 1995, which is a CIP of U.S. Application Ser. No. 08/267,641, filed Jun. 24, 1994, now abandoned.

The invention is drawn to antibodies that bind to insect gut proteins and their use, particularly their use in creating new hybrid toxin molecules. The invention further relates to microorganisms, plant cells and plants producing the said antibodies and hybrid toxins, respectively. The invention also encompasses insecticidal compositions and the use thereof in protecting plants against insect pests.

BACKGROUND OF THE INVENTION

Control of various pests through the use of biological molecules has been possible in only a limited number of cases. The best known examples of biological molecules with pesticidal uses are the δ-endotoxins from *Bacillus thuringiensis* (Bt). Various strains of Bt are known which produce insecticidal proteins, the δ-endotoxins, during sporulation. Some of these δ-endotoxins have useful insecticidal activities against different insect pests. However, use of the δ-endotoxins is limited because they are active against only a very few of the many insect pests.

The limited specificity of the Bt endotoxins is dependent, at least in part, on both the activation of the toxin in the insect gut (Haider, M. Z. et al., 1986, Eur. J. Biochem. 156:531–540) and its ability to bind to specific receptors present on the insect's midgut epithelial cells (Hofmann, C. P. et al., 1988, PNAS 85:7844–7848). Among the factors which prevent activity of a particular Bt δ-endotoxin against a specific insect is the lack of appropriate receptors in the insect gut or lack of affinity of the δ-endotoxin for the receptors which may be present, thus resulting in no binding of the δ-endotoxin to the brush border membranes. Therefore, the ability to control a specific insect pest using Bt δ-endotoxins at present depends on the ability to find an appropriate δ-endotoxin with the desired range of activity. In many cases, no such δ-endotoxin is known, and it is not certain that one even exists. For example, thousands of Bt strains have been screened for activity against western corn rootworm (WCRW), a major pest of maize. However, to date there are no reports of strains of Bt which produce a δ-endotoxin that is highly effective against WCRW.

Individual δ-endotoxins typically have a very narrow spectrum of activity, each being active against only one or a few insect pests. Moreover, the δ-endotoxins have been shown to be active against only a few members of but a small number of Orders of insects. The ability to produce additional proteins with unique pesticidal activities creates more options for the control of agricultural pests, particularly insects, using biological molecules with a high level of safety for non-target organisms. Thus, there is a need for binding proteins which can be designed to target a particular insect pest.

SUMMARY OF THE INVENTION

Hence, the present invention is drawn to antibodies, but especially to monoclonal antibodies or fragments thereof which bind to brush border membrane vesicles of the insect gut and to the gene or genes which encode these proteins. The antibodies according to the invention bind to proteins in the gut of a target insect especially to a target insect selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, and Trichoptera but do not bind to mammalian brush border membranes or to plant microsomes. In particular the invention relates to a monoclonal antibody or fragment which binds to the gut of the western corn root worm. In a preferred embodiment, the invention relates to a monoclonal antibody which is selected from the group consisting of 2B5, 3B1, 10B6, 17F6, 14G1 and 16E4.

Also comprised by the invention are hybridoma cell lines producing the monoclonal antibodies according to the invention, but in particular hybridoma cell lines which have been deposited under accession number ATCC HB 11616, HB 11617, HB 11618, HB 11619 and HB 11620.

It is a further object of the invention to provide a DNA sequence which encodes a monoclonal antibody or the binding site of said monoclonal antibody according to the invention. In particular the invention relates to a DNA sequence encoding a monoclonal antibody or the binding fragment thereof wherein said DNA sequence is selected from SEQ. ID Nos 1, 3, 5, 7, 9, 11, 13, 15, 17, 44 or 46. Also included is a DNA sequence wherein said DNA sequence is operably linked to a toxin moiety, especially wherein said toxin moiety is selected from Bacillus toxins, Pseudomonas exotoxin, phytolaccin, gelonin, ribonucleases or ribosome inactivating proteins.

The antibodies and the genes encoding them may find use in constructing hybrid-toxins for control of insect pests. Hence, an additional aspect of the invention is a hybrid toxin molecule comprising the monoclonal antibody or monoclonal antibody binding fragment according to the invention operably linked with a toxin moiety. In a preferred embodiment of the invention the said toxin moiety is selected from Bacillus toxins such as, for example, Bacillus endotoxins but especially from toxins selected from the group consisting of Bt endotoxin, vegetative insecticidal proteins, Pseudomonas exotoxin, phytolaccin, gelonin, ribonucleases andr ribosome inactivating proteins.

The invention thus further relates to a hybrid toxin comprising a monoclonal antibody or binding region thereof which binds to the gut of a target insect but especially to insect brush border membranes but does not bind to mammalian brush border membranes or to plant microsomes operably linked to a toxin moiety wherein the toxin moiety is selected from Bacillus toxins such as, for example, Bacillus endotoxins but especially from toxins selected from the group consisting of Bt endotoxin, vegetative insecticidal proteins, Pseudomonas exotoxin, phytolaccin, gelonin, ribonucleases andr ribosome inactivating proteins.

The invention further encompasses a DNA sequence which encodes a hybrid toxin according to the invention comprising a monoclonal antibody or binding region thereof which binds to the gut of a target insect but does not bind to mammalian brush border membranes or to plant microsomes operably linked to a toxin moiety.

The invention further encompasses a microbial host which is transformed with a suitable vector in which a DNA molecule encoding the hybrid toxin according to the invention is inserted. In particular the microbial host includes bacteria, algae and fungi.

The present invention thus further comprises a recombinant microorganism, but especially a microorganism selected from the group consisting of bacteria such as Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, such as Saccharomyces, Cryptococcus, Kluyveromyces, Sporobolomyces, Rhodotorula, and Aureobasidium and viruses such as the nuclear polyhedrosis virus *Autographica californica,* transformed with at least one of the DNA sequences according to the invention.

In particular, the invention relates to a recombinant microorganism comprising at least one DNA molecule encoding a hybrid toxin comprising an antibody or fragment thereof which binds to the gut of a target insect but does not bind to mammalian brush border membranes or to plant microsomes operably linked to a toxin moiety wherein the said DNA encoding a monoclonal antibody comprises a sequence selected from the group consisting of SEQ. ID Nos 1, 3, 5, 7, 9, 11, 13, 15, 17, 44 or 46.

The invention further encompassess an entomocidal composition comprising any of the above mentioned recombinant microorganisms according to the invention in an insecticidally-effective amount together with a suitable carrier.

In particular, the invention relates to an entomocidal composition comprising an isolated hybrid toxin molecule according to the invention in an insecticidally-effective amount together with a suitable carrier.

The invention further relates to a DNA sequence consisting of a first expression cassette comprising a DNA sequence which encodes a promoter capable of directing expression in a plant operably linked to a first DNA sequence which encodes a light chain of a monoclonal antibody or antibody binding domain wherein said monoclonal antibody binds the gut of a target insect. In a further embodiment said cassette further comprises a second DNA sequence which encodes a toxin moiety operably linked to the said first DNA sequence which encodes the light chain of the monoclonal antibody or antibody binding domain. Especially preferred is an expression cassette wherein the second DNA sequence encodes a toxin moiety selected from the group consisiting of Bacillus toxins, Pseudomonas exotoxin, phytolaccin, gelonin, ribonucleases andr ribosome inactivating proteins.

The invention further encompasses a DNA sequence comprising a second expression cassette comprising a DNA sequence encoding a promoter capable of directing expression in a plant operably linked to a first DNA sequence which encodes a heavy chain of a monoclonal antibody or antibody binding domain wherein said monoclonal antibody binds the gut of a target insect. In a further embodiment said cassette further comprises a second DNA sequence which encodes a toxin moiety operably linked to the said first DNA sequence encoding the heavy chain of the monoclonal antibody or antibody binding domain. Especially preferred is an expression cassette wherein the second DNA sequence encodes a toxin moiety selected from the group consisiting of Bacillus toxins, Pseudomonas exotoxin, phytolaccin, gelonin, ribonucleases andr ribosome inactivating proteins.

The DNA sequence according to the invention my be present either in an isolated and essentially purified form or as part of a plant genome.

The invention further relates to plant cells or plants including the progeny thereof, but especially to maize plants, which plant cells or plants are transformed with a DNA sequence according to the invention, but especially with a plant expression cassette according to the invention. The invention further embodies transgenic plant cells or plants including the progeny thereof, but especially maize plants, which express a hybrid toxin according to the invention, especially in an amount sufficient to render the plant cell and plant, respectively, tolerant or resistant to insect pests. The plants according to the invention are preferably hybrid plants.

Also comprised within the scope of the invention are plant propagules but especially plant seeds that are treated with a protectant coating.

The invention further relates to a process for the preparation of a hybridoma cell line which produces an antibody or monoclonal antibody according to the invention comprising a) utilizing insect guts, particularly insect brush border membranes, as the antigen;
b) immunising a donor animal with said antigen;
c) isolating an immunocompetent B cell from the immunised donor animal;
d) fusing said immunocompetent B cell with a tumour cell line which is capable of continuous cell division;
e) isolating the resulting fusion product, cultivating it in a suitable culture medium and subsequently cloning positive hybrid cells; and
f) screening the cloned hybrid cells for the production of monoclonal antibodies, and selecting those which show the required properties.

The invention further relates to a method of producing an antibody, but especially a monoclonal antibody or fragments thereof which bind to brush border membrane vesicles of insect gut comprising growing the hybridoma cell lines producing the said antibodies in a suitable cultivation medium in vivo or in vitro and isolating the resulting antibodies.

The invention further relates to a method of producing hybrid toxins comprising the monoclonal antibody or monoclonal antibody binding fragment according to the invention operably linked with a toxin moiety which bind to brush border membrane vesicles of the insect gut comprising cloning the variable region of the said antibodies and linking said region to the toxin moiety.

Further comprised by the invention is a process of producing a DNA sequence encoding a monoclonal antibody according to the invention comprising cloning the respective antibody genes from hybridoma cells using primers to conserved DNA sequences within the constant regions and the framework regions of the variable regions.

The invention further encompases a method of producing a transgenic plant cell and plant, respectively comprising transforming the said plant cell or plant with one or more of the aforementioned DNA sequences encoding a hybrid toxin according to the invention comprising a monoclonal antibody or binding region thereof which binds to the gut of a target insect but does not bind to mammalian brush border membranes or to plant microsomes operably linked to a toxin moiety.

BRIEF DESCRIPTION OF THE DRAWING

FIG. 1: Western blot analysis of binding of monoclonal antibodies to corn rootworm brush border membrane vesicles after electrophoresis on acrylamide gels. Antibodies from cell lines 3B1, 2B5, 17F6 and 10B6 were used in the analysis. MW=Molecular weight standards.

DETAILED DESCRIPTION OF THE INVENTION

Antibodies and monoclonal antibodies, including fragments thereof which are capable of binding with the specificity of the antibody or monoclonal antibody, to proteins found in the insect gut are provided. Such antibodies bind to insect gut cells but do not bind to mammalian brush border membrane vesicles (BBMVs), nor to plant microsomes.

The antibodies of the invention include polyclonal and monoclonal antibodies as well as fragments thereof which retain their ability to bind to proteins found in the insect gut. An antibody, monoclonal antibody, or fragment thereof is said to be capable of binding a molecule if it is capable of specifically reacting with the molecule to thereby bind the molecule to the antibody, monoclonal antibody, or fragment thereof. The term "antibody" (Ab) or "monoclonal antibody" (Mab) is meant to include intact molecules as well as fragments or binding regions or domains thereof (such as, for example, Fab and F(ab)$_2$ fragments) which are capable of binding hapten. Such fragments are typically produced by proteolytic cleavage, such as papain or pepsin. Alternatively, hapten-binding fragments can be produced through the application of recombinant DNA technology or through synthetic chemistry.

Methods for the preparation of the antibodies of the present invention are generally known in the art. For example, see *Antibodies, A Laboratory Manual*, Ed Harlow and David Lane (eds.) Cold Spring Harbor Laboratory, NY (1988), as well as the references cited therein. Standard reference works setting forth the general principles of immunology include: Klein, J. *Immunology: The Science of Cell-Noncell Discrimination*, John Wiley & Sons, NY (1982); Dennett, R., et al. *Monoclonal Antibodies, Mybridoma: A New Dimension in Biological Analyses*, Plenum Press, NY (1980); and Campbell, A. "Monoclonal Antibody Technology," *In Laboratory Techniques in Biochemistry and Molecular Biology*, Vol. 13, Burdon et al. (eds.), Elsevier, Amsterdam (1984). See also, U.S. Pat. Nos: 4,609,893; 4,713,325; 4,714,681; 4,716,111; 4,716,117; and 4,720,459.

The antibody and monoclonal antibodies of the present invention can be prepared by utilizing insect guts, particularly insect brush border membranes, as the antigen. Such insect gut membranes can be prepared by methods known in the art. Generally, brush border membranes can be isolated from insect larvae by dissection of guts and homogenization followed by calcium chloride precipitation of membranes. See, for example, Wolfersberger (1986) Comp. Biochem. Physiol. 86A:301–308.

It is recognized that following the methods described herein, antibodies specific for a particular target insect can be prepared. By target insect is meant an insect in which the antibodies of the present invention will bind to protein or proteins present in the gut. That is, antibodies can be prepared that are capable of binding proteins present in the gut of only the target insect.

The target insect encompasses any insect including insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc. Thus, any insect pest can be selected and antibodies made which are specific to that insect. Of particular interest are insect pests for which there is no Bt protein which is capable of binding and killing, such as western corn rootworm.

The antibody and monoclonal antibody producing cell lines of the invention are a subset of all monoclonal antibodies produced when insect brush border membrane vesicles (BBMVs) are used as antigen for the production of MAb lines. The binding characteristics of the desired monoclonal antibody producing cell lines are determined by differentially screening all of the various monoclonal antibodies raised against the BBMVs of the target insect.

The differential screen of the present invention identifies the antibody lines which also bind mammalian BBMVs and/or microsomes of plants. MAb cell lines which bind to mammalian BBMVs or to plant microsomes are discarded. A differential screen can also identify Mab cell lines which bind BBMV of insects in species other than the target insect. Thus, the antibodies of the invention are those which demonstrate highly selective binding for only target insects, especially for the gut of a target insect.

The subset of MAb lines which possess the desired binding specificity can be used as a source of messenger RNA for cloning of the cDNA for the particular monoclonal antibody. Antibody genes can be cloned from hybridoma cells using primers to conserved DNA sequences within the constant regions and the framework regions of the variable regions. This can be followed by amplification of the DNA for cloning using the polymerase chain reaction (PCR). A database of mouse heavy chain and light chain sequences complied by Kabat et al. has been successfully used to generate both isotype specific and degenerate primers for cloning antibody genes (Kabat, E. A. et al., 1987, US Dept Health and Human Services, US Government Printing Offices and Jones, S. T. and Bendig, M., 1991, Bio/technology 9:88–89). Additionally, there is a wealth of knowledge concerning the cloning of smaller fragments of antibodies which possess the binding properties of the original antibody.

The cloned DNA can then be sequenced by methods known in the art. See, for example, Sambrook et al., Molecular Cloning: A Laboratory Manual, 2nd. Edition, Cold Spring Harbor Laboratory Press, NY (1989) vol. 1–3, and the references cited therein. From the nucleic acid sequence, the protein sequence of the binding region from the selected MAb can be deduced.

The antibodies and monoclonal antibodies of the invention find use in the production of hybrid toxin molecules. By "hybrid toxin molecules" or "hybrid toxins" is intended, fusion proteins or immunotoxins, which comprise a monoclonal antibody or antibody fragment operably linked to a toxin moiety and which is capable of binding to the gut of an insect. That is, when linked, the monoclonal antibody or antibody fragment retains its binding properties and the toxin moiety retains its cytotoxic properties.

A number of cytotoxic proteins can be utilized as the toxin moiety. These include but are not limited to Bacillus toxins, including endotoxins and vegetative insecticidal proteins. See for example U.S. application Ser. No. 08/037,057, filed Mar. 25, 1993 and WO 93/07278, herein incorporated by reference. Other toxins include catalytic ribosome inactivators such as gelonin, Pseudomonas exotoxin A or phytolaccin, (the structure of Pseudomonas exotoxin has been well characterized in Chaudhary et al., (1990) J. Biol. Chem. 265:16303–16310); cell metabolism disrupters, such as ribonucleases, (see, for example, Mariani et al. (1990) Nature 347:737–741); Barnase toxin (or PE-Bar), a chimeric toxin derived from Pseudomonas exotoxin A and a ribonuclease, (see, Prior et al. (1991) Cell 64:1017–1023); hydrophilic peptides that create pores in membranes (see, Frohlich and Wells (1991) Int. J. Peptide Protein Res. 37:2–6); etc.

The hybrid toxin molecules of the present invention therefore contain a region which allows binding of the molecule to insect guts (antibody region) as well as a toxic region to effect killing of the targeted cell and ultimately the targeted insect. By utilizing the monoclonal antibodies or fragments thereof in the hybrid toxins, the hybrid toxins bind to the gut of a target insect and thereby exert a toxic effect on only that insect. The binding characteristics of such hybrid toxins are derived from the MAb binding region while the toxic effect of such hybrid toxins is derived from the toxic moiety used.

Methods for linking the antibody or antibody fragments to the toxins are known in the art. Such methods include linkers used in single chain antibody immunotoxins (Chaudhary et al. (1989) Nature 339:394–397; Chaudhary et al. (1990) PNAS 87:9491–9494; Batra etal. 1991, Mol. and Cellular Biol. 11:2200–2205; Brinkmann, et al. (1991), PNAS 88:8616–8620; Brinkmann et al. (1992) PNAS 89:3075–3079; Whitlow et al. (1993) Protein Engineering 6:989–995). One particularly useful linker is based on the human IgA1 hinge region as reported by Hallewell et al. (1989) J. Biol. Chem. 264: 5260–5268 and described in SEQ ID NO: 43.

The activity of the hybrid toxin molecules may depend on several factors which can be optimized. The activity can be assayed using protein produced by transiently expressing maize protoplasts. In this manner, maize protoplasts expressing the hybrid toxins can be incorporated into insect diet for activity assays. For general insect assays, see Marrone (1985) J. Econ. Entomolo. 78:290–293, MacIntosh et. at. (1990) J. of Invertebrate Pathology 56:258–266 and the references cited therein.

Thus, hybrid toxin constructs can be tested for insecticidal activity against the target pest of interest. Those constructs exhibiting activity can be further developed for agricultural use.

It is further recognized that various constructs of hybrid toxins can be generated. For example, the hybrid toxin could be encoded by two expression cassettes which respectively encode the light and heavy chains of the antibody molecule. This binary hybrid toxin can then be assembled in vivo using the normal processing machinery of the cell to create the antibody binding site. The toxin moiety of the hybrid can be operably linked to the N or C terminal of the light or heavy chain or alternatively could replace any or part of the constant regions of either chains. The toxin moiety could also be inserted within a constant region or between constant regions of the antibody chains. Such constructions can be made by standard molecular techniques. See, for example Sambrook et al., Molecular Cloning: A Laboratory Manual, 2nd. Edition, Cold Spring Harbor Laboratory Press, NY (1989) vol. 1–3 and the references cited therein.

The hybrid toxins of the present invention, including binary toxins, can be produced in plants. In this manner, the antibody genes can be cloned and expressed in plants in such a manner that functional antibodies are assembled. See, for example, Hiatt et al. (1989) Nature 342:76–78 During et al. (1990) J. Plant Molecular Biology 15:281–293 and PCT Application WO 91/06320. Levels of bivalent antibody expression have been reported to be as high as 1% of the soluble protein in tobacco. It is recognized that as well as antibody molecules, antibody fragments such as Fab and Fv fragments, can be utilized. The smaller Fab and Fv antigen-binding fragments (12 kDa–50 kDa) have been shown to retain full binding affinity. Single chain Fv fragments (scFv), in which Vh and VI domains are linked by a hydrophilic and flexible peptide, have been used successfully to target enzymes and toxins to specific cells (Bird (1988) Science 423:423426 and Huston (1988) PNAS 85:5879–5883). Single Vh domains (Dabs) and single complementary determining regions as small as 20 amino acids (aa) called minimal recognition units (mru) have also been used for antigen binding (Ward (1989) Nature 341:544–546 and Taub (1989) J. Biol. Chem 264:259–265 and Williams (1989) PNAS 86:5537–5541). The use of these antibody fragments provides the option of reducing the insect specific binding domain derived from a MAb to a very small size.

DNA fragments encoding antibodies, or regions of antibodies, which bind to the gut of insects are also encompassed by the present invention. In a preferred embodiment, these DNA fragments encode binding regions which are derived from monoclonal antibodies raised against BBMVs of a desired target insect and screened to ensure they do not bind to mammalian BBMV or to plant microsomes. Such DNA fragments can be used in the construction of genes encoding novel hybrid toxin molecules which are discussed above.

DNA sequences encoding the toxin moiety of the hybrid toxins are known in the art. See, Lamb et al. (1985) Eur. J. Biochem. 148:275–170 (Ricin); Gray etal. (1984) PNAS 81:2645–2649 (Pseudomonas toxin DNA Sequence); Hindley and Berry (1988) Nuc. Acids Res. 16:4168 (*B. sphaericus* toxin gene); Bauman et al. (1988) J. Bacteriol. 170:2045–2050, Baumann et al. 1987) J. Bacteriol. 169:4061–4067, Berry and Hindley (1987) Nucleic Acids Res. 15:5891, Berry et al. (1989) Nucleic Acids Res. 17:7516 (B. sphaericus); WO 9309130-A (gelonin); EP 466222-A, U.S. Pat. No. 5,128,460 (ribosome-activating protein); EP 412911-A (barnase); Heemstadt etal. (1987) Gene 57:37–46 (cryIIIA); Brizzard and Whiteley (1988) Nucleic Acids Res 16:2723–2724 (cryIB); and Geiser et al. (1986) Gene 48:109–118 (crIAA(b)). See also Porter et al. (1 993) Microbiological Reviews 57:838–861; Hofte and Whiteley (1989) Microbiological Reviews 53:242–255; and WO 93/07278.

The hybrid toxin genes of the invention can be optimized for enhanced expression in plants. See, for example WO 93/07278; EPA 0359472; EPA 0385962; WO 91/16432; Perlak et al. (1991) Proc. Natl. Acad. Sci. USA 88:3324–3328; and Murray (1989) Nucleic Acids Research 17: 477498. In this manner, the genes can be synthesized utilizing plant preferred codons. That is, the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray, (1989), Nucleic Acids Research 17:477–498, the disclosure of which is incorporated herein by reference. Synthetic genes could also be made based on the distribution of codons a particular host uses for a particular amino acid.

Following this approach, the nucleotide sequences can be optimized for expression in any plant. It is recognized that all or any part of the gene sequence may be optimized or synthetic. That is, synthetic, partially optimized, or native sequences may also be used.

Methods for the transformation of plant cells and regeneration of transformed plants are well known in the art. Generally, for the introduction of foreign DNA into plants Ti plasmid vectors have been utilized as well as direct DNA uptake, liposomes, electroporation, micro-injection, and the use of microprojectiles. Such methods have been published. See, for example, Guerche et al., (1987) Plant Science 52:111–116; Neuhause et al., (1987) Theor. Appl. Genet. 75:30–36; Klein etal., (1987) Nature 327: 70–73; Howell et al., (1980) Science 208:1265; Horsch et al., (1985) Science 227: 1229–1231; DeBlock et al., (1989) Plant Physiology 91:694–701; Methods for Plant Molecular Biology (Weissbach and Weissbach, eds.) Academic Press, Inc. (1988); and Methods in Plant Molecular Biology (Schuler and Zielinski, eds.) Academic Press, Inc. (1989). See also, EPA 0193259 and EPA 0451878A1. It is understood that the method of transformation will depend upon the plant cell to be transformed.

It is further recognized that the components of an expression cassette containing the sequence of interest may be modified to increase expression in the plant or plant cell. For example, truncated sequences, nucleotide substitutions or other modifications may be employed. See, for example Perlak et al. (1991) Proc. Natl. Acad. Sci. USA 88:3324–3328; Murray et al. (1989) Nucleic Acids Research 17:477–498; and WO 91/16432.

The construct may also include any other necessary regulators such as terminators, (Guerineau et al., (1991), Mol. Gen. Genet., 226:141–144; Proudfoot, (1991), Cell, 64:671–674; Sanfacon et al., (1991), Genes Dev., 5:141–149; Mogen et al., (1990), Plant Cell, 2:1261–1272; Munroe et al., (1990), Gene, 91:151–158; Ballas et al., (1989), Nucleic Acids Res., 17:7891–7903; Joshi et al., (1987), Nucleic Acid Res., 15:9627–9639); plant translational consensus sequences (Joshi, C. P., (1987), Nucleic Acids Research, 15:6643–6653), introns (Luehrsen and Walbot, (1991), Mol. Gen. Genet., 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (Encephalomyocarditis 5' noncoding region) (Elroy-Stein, O., Fuerst, T. R., and Moss, B. (1989) PNAS USA 86:6126–6130);

Potyvirus leaders, for example, TEV leader (Tobacco Etch Virus) (Allison et al., (1986); MDMV leader (Maize Dwarf Mosaic Virus); Virology, 154:9–20), and Human immunoglobulin heavy-chain binding protein (BiP), (Macejak, D. G., and Sarnow, P., (1991), Nature, 353:90–94;

Untranslated leader from the coat protein mRNA of alfalfa mosaic virus (AMV RNA 4), (Jobling, S. A., and Gehrke, L., (1987), Nature, 325:622–625;

Tobacco mosaic virus leader (TMV), (Gallie, D. R. et al., (1989), Molecular Biology of RNA, pages 237–256; and Maize Chlorotic Mottle Virus leader (MCMV) (Lommel, S. A. et al., (1991), Virology, 81:382–385. See also, Della-Cioppa et al., (1987), Plant Physiology, 84:965–968.

A plant terminator may be utilized in the expression cassette. See, Rosenberg et al., (1987), Gene, 56:125; Guerineau et al., (1991), Mol. Gen. Genet., 226:141–144; Proudfoot, (1991), Cell, 64:671–674; Sanfacon et al., (1991), Genes Dev., 5:141–149; Mogen et al., (1990), Plant Cell, 2:1261–1272; Munroe et al., (1990), Gene, 91:151–158; Ballas et al., (1989), Nucleic Acids Res., 17:7891–7903; Joshi et al., (1987), Nucleic Acid Res., 15:9627–9639.

For tissue specific expression, the nucleotide sequences of the invention can be operably linked to tissue specific promoters. See, for example, U.S. WO 93/07278 herein incorporated by reference.

Further comprised within the scope of the present invention are transgenic plants, in particular transgenic fertile plants transformed by means of the aforedescribed processes and their asexual and/or sexual progeny, which still comprises a DNA molecule encoding a monoclonal antibody or a hybrid toxin according to the invention. Mature plants that have been raised from the transformed plant material according to the invention, are either selfed or outcrossed for the production of seeds.

The transgenic plant according to the invention may be a dicotyledonous or a monocotyledonous plant. Preferred are monocotyledonous plants of the Graminaceae family involving Lolium, Zea, Triticum, Triticale, Sorghum, Saccharum, Bromus, Oryzae, Avena, Hordeum, Secale and Setaria plants.

Especially preferred are transgenic maize, wheat, barley, sorghum, rye, oats, turf grasses and rice.

Among the dicotyledonous plants soybean, cotton, tobacco, sugar beet, oilseed rape, and sunflower are especially preferred herein.

The expression 'progeny' is understood to embrace both, "asexually" and "sexually" generated progeny of transgenic plants. This definition is also meant to include all mutants and variants obtainable by means of known processes, such as for example cell fusion or mutant selection and which still exhibit the characteristic properties of the initial transformed plant, together with all crossing and fusion products of the transformed plant material.

Another object of the invention concerns the proliferation material of transgenic plants.

The proliferation material of transgenic plants is defined relative to the invention as any plant material that may be propagated sexually or asexually in vivo or in vitro. Particularly preferred within the scope of the present invention are protoplasts, cells, calli, tissues, organs, seeds, embryos, pollen, egg cells, zygotes, tubers, grains, fruit, together with any other propagating material obtained from transgenic plants.

Parts of plants, such as for example flowers, stems, fruits, leaves, roots originating in transgenic plants or their progeny previously transformed by means of the process of the invention and therefore consisting at least in part of transgenic cells, are also an object of the present invention.

Before the plant propagation material [fruit, tuber, grains, seed], but expecially seed is sold as a commerical product, it is customarily treated with a protectant coating comprising herbicides, insecticides, fungicides, bactericides, nematicides, molluscicides or mixtures of several of these preparations, if desired together with further carriers, surfactants or application-promoting adjuvants customarily employed in the art of formulation to provide protection against damage caused by bacterial, fungal or animal pests.

In order to treat the seed, the protectant coating may be applied to the seeds either by impregnating the tubers or grains with a liquid formulation or by coating them with a combined wet or dry formulation. In addition, in special cases, other methods of application to plants are possible, eg treatment directed at the buds or the fruit.

The plant seed according to the invention comprising a DNA sequence encoding a monoclonal antibody or a hybrid toxin according to the invention may be treated with a seed protectant coating comprising a seed treatment compound, such as, for example, captan, carboxin, thiram (TMTD®), methalaxyl (Apron®) and pirimiphos-methyl (Actellic®) and others that are commonly used in seed treatment.

It is thus a further object of the present invention to provide plant propagation material for cultivated plants, but especially plant seed that is treated with an seed protectant coating customarily used in seed treatment.

The hybrid toxin proteins of the invention may be used for protecting agricultural crops and products from pests.

Alternatively, a gene encoding the hybrid toxin may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli* and *Azotobacter vinlandii,* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans.* Of particular interest are the pigmented microorganisms.

The utility of the novel toxin hybrid genes present in a recombinant strain of microorganism is illustrated in Example 7. It should also be recognized that the isolated novel toxin hybrid gene of the present invention can be transferred into any microbial host and confer their insecticidal properties upon that host. Alternate hosts for the novel toxin hybrid gene of the present invention can be selected as suitable for cloning purposes, for purposes of characterizing the form and function of the gene or encoded protein, for use as a fermentation host to increase production of the toxin hybrid protein, for purposes of delivering at least one of the toxin hybrid proteins more effectively to the target insect pest, or introduction of the novel toxin hybrid gene into insect pathogens such as baculovirus [a nuclear polyhedrosis virus, eg [*Autographica californica*] to improve their effectiveness.

The novel toxin hybrid genes or recombinant forms thereof can be transformed into such alternate hosts using a variety of art recognized methods. One such preferred method is electroporation of microbial cells, as described, for example, by the method of Dower (U.S. Pat. No. 5,186,800). Another preferred method is that of Schurter et al. (Mol. Gen. Genet. 218: 177–181 (1989)), which is also disclosed in EP-A 0 342 633 which is incorporated herein in its entirety.

It is envisioned that said alternate host would be applied to the environment or plants or animals for insect control. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

The present invention further provides an entomocidal composition comprising as an active ingredient at least one of the novel toxin hybrids according to the invention or a recombinant microorganism containing at least on of the novel toxin genes in recombinant form together with an agricultural adjuvant such as a carrier, diluent, surfactant or application-promoting adjuvant. The composition may also contain a further biologically active compound. The said compound can be both a fertilizer or micronutrient donor or other preparations that influence plant growth. It can also be a selective herbicide, insecticide, fungicide, bactericide, nematicide, molluscide or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers The composition may comprise from 0.1 to 99% by weight of the active ingredient, from 1 to 99.9% by weight of a solid or liquid adjuvant, and from 0 to 25% by weight of a surfactant. The acitve ingredient comprising at least one of the novel toxin hybrid toxins according to the invention or a recombinant microorganism containing at least one of the novel toxin genes in recombinant form or the composition containing the said acitve ingredient, may be administered to the plants or crops to be protected together with certain other insecticides or chemicals (1993 Crop Protection Chemicals Reference, Chemical and Pharmaceutical Press, Canada) without loss of potency. It may be administered as a dust, a suspension, a wettable powder or in any other material form suitable for agricultural application.

The invention further provides methods for for controlling or inhibiting of insect pests by applying an active ingredient comprising at least one of the novel toxin hybrids according to the invention or a recombinant microorganism containing at least one of the novel toxin hybrid gene in recombinant form or a composition comprising the said active ingredient to (a) an environment in which the insect pest may occur, (b) a plant or plant part in order to protect said plant or plant part from damage caused by an insect pest, or (c) seed in order to protect a plant which develops from said seed from damage caused by an insect pest. A preferred method of application in the area of plant protection is application to the foliage of the plants (foliar application), with the number of applications and the rate of application depending on the plant to be protected and the risk of infestation by the pest in question. However, the active ingredient may also penetrate the plants through the roots (systemic action) if the locus of the plants is impregnated with a liquid formulation or if the active ingredient is incorporated in solid form into the locus of the plants, for example into the soil, e.g. in granular form (soil application). In paddy rice crops, such granules may be applied in metered amounts to the flooded rice field.

The compositions according to the invention are also suitable for protecting plant propagating material, e.g. seed, such as fruit, tubers or grains, or plant cuttings, from insect pests. The propagation material can be treated with the formulation before planting: seed, for example, can be dressed before being sown. The acitve ingredient of the invention can also be applied to grains (coating), either by impregnating the grains with a liquid formulation or by coating them with a solid formulation. The formulation can also be applied to the planting site when the propagating material is being planted, for example to the seed furrow during sowing. The invention relates also to those methods of treating plant propagation material and to the plant propagation material thus treated.

The compositions according to the invention comprising as an active ingredient a recombinant microorganism containing at least one of the novel toxin hybrid genes in recombinant form may be applied in any method known for treatment of seed or soil with bacterial strains. For example, see U.S. Pat. No. 4,863,866. The strains are effective for biocontrol even if the microorganism is not living. Preferred is, however, the application of the living microorganism.

Target crops to be protected within the scope of the present invention comprise, e.g., the following species of plants:

cereals (wheat, barley, rye, oats, rice, sorghum and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

A recombinant microorganism containing at least one of the novel gene in recombinant form is normally applied in the form of entomocidal compositions and can be applied to the crop area or plant to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation.

The active ingredient according to the invention may be used in unmodified form or together with any suitable agriculturally acceptable carrier. Such carriers are adjuvants conventionally employed in the art of agricultural formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objective and the prevailing circumstances. Advantageous rates of application are normally from about 50 g to about 5 kg of active ingredient (a.i.) per hectare ("ha", approximately 2.471 acres), preferably from about 100 g to about 2 kg a.i./ha. Important rates of application are about 200 g to about 1 kg a.i./ha and 200 g to 500 g a.i./ha. For seed dressing advantageous application rates are 0.5 g to 1000 g a.i.per 100 kg seed, preferably 3 g to 100 g a.i. per 100 kg seed or 10 g to 50 g a.i.per 100 kg seed.

Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The formulations, i.e. the entomocidal compositions, preparations or mixtures containing the recombinant microorganism containing the novel gene in recombinant form as an active ingredient or combinations thereof with other active ingredients, and, where appropriate, a solid or liquid adjuvant, are prepared in known manner, e.g., by homogeneously mixing and/or grinding the active ingredients with extenders, e.g., solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used, e.g., for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates. The fatty sulfonates or sulfates are usually in the forms of alkali metal salts, alkaline earth metal salts or unsubstituted or substituted ammonium salts and generally contain a $C_8$–$C_{22}$ alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactant are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$ alkyl radical and, as further substituents, lower unsubstituted or halogenated alkyl, benzyl or hydroxyl-lower alkyl radicals. The salts are preferably in the form of halides, methylsulfates or ethylsulfates, e.g., stearyltrimethylammonium chloride or benzyldi-(2-chloroethyl) ethylammonium bromide.

The surfactants customarily employed in the art of formulation are described, e.g., in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna.

Another particularly preferred characteristic of an entomocidal composition of the present invention is the persistence of the active ingredient when applied to plants and soil. Possible causes for loss of activity include inactivation by ultra-violet light, heat, leaf exudates and pH. Formulation of an entomocidal composition of the present invention can address these problems by either including additives to help prevent loss of the active ingredient or encapsulating the material in such a way that the active ingredient is protected from inactivation. Encapsulation can be accomplished chemically (McGuire and Shasha, J Econ Entomol 85: 1425–1433, 1992) or biologically (Barnes and Cummings, 1986; EP-A 0 192 319). Chemical encapsulation involves a process in which the active ingredient is coated with a polymer while biological encapsulation involves the expression of the hybrid toxin genes in a microbe. For biological encapsulation, the intact microbe containing the hybrid toxin protein is used as the active ingredient in the formulation. The addition of UV protectants might effectively reduce irradiation damage. Inactivation due to heat could also be controlled by including an appropriate additive.

Preferred within the present application are formulations comprising living microorganisms as active ingredient either in form of the vegetative cell or more preferable in form of spores, if available. Suitable formulations may consist, for example, of polymer gels which are crosslinked with polyvalent cations and comprise these microorganisms. This is described, for example, by D. R. Fravel et al. in Phytopathology, Vol. 75, No. 7, 774–777,1985 for alginate as the polymer material. It is also known from this publication that carrier materials can be co-used. These formulations are as a rule prepared by mixing solutions of naturally occurring or synthetic gel-forming polymers, for example alginates, and aqueous salt solutions of polyvalent metal ions such that individual droplets form, it being possible for the microorganisms to be suspended in one of the two or in both reaction solutions. Gel formation starts with the mixing in drop form. Subsequent drying of these gel particles is possible. This-process is called ionotropic gelling. Depending on the degree of drying, compact and hard particles of polymers which are structurally crosslinked via polyvalent cations and comprise the microorganisms and a carrier present predominantly uniformly distributed are formed. The size of the particles can be up to 5 mm.

Compositions based on partly crosslinked polysaccharides which, in addition to a microorganism, for example, can also comprise finely divided silicic acid as the carrier material, crosslinking taking place, for example, via $Ca^{++}$ ions, are described in EP-A1-0 097 571. The compositions have a water activity of not more than 0.3. W. J. Cornick et al. describe in a review article [New Directions in Biological Control: Alternatives for Suppressing Agricultural Pests and Diseases, pages 345–372, Alan R. Liss, Inc. (1990)] various formulation systems, granules with vermiculite as the carrier and compact alginate beads prepared by the ionotropic gelling process being mentioned. Such compositions are also disclosed by D. R. Fravel in Pesticide Formulations and Application Systems: 11 th Volume, ASTM STP 1112 American Society for Testing and Materials, Philadelphia, 1992, pages 173 to 179 and can be used to formulate the recombinant microorganisms according to the invention.

The entomocidal compositions of the invention usually contain from about 0.1 to about 99%, preferably about 0.1 to about 95%, and most preferably from about 3 to about 90% of the active ingredient, from about 1 to about 99.9%, preferably from about 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

In a preferred embodiment of the invention the entomocidal compositions usually contain 0.1 to 99%, preferably 0.1 to 95%, of a recombinant microorganism containing at least one of the novel genes in recombinant form, or combination thereof with other active ingredients, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration. The entomocidal compositions may also contain further ingredients, such as stabilizers, antifoams, viscosity regulators, binders, tackifiers as well as fertilizers or other active ingredients in order to obtain special effects.

A number of ways are available for introducing a gene expressing the hybrid toxin into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis etal. (eds.) Cold Spring Harbor Laboratory, Cold Spring Harbor, N.Y. (1980); and the references cited therein.

The following examples are offered by way of illustration and are not meant to be limiting on the invention described herein.

EXPERIMENTAL

EXAMPLE 1

Monoclonal Antibody Development 1.1. Immunization:

Appropriate quantities of the antigen (approximately 50 micrograms of corn rootworm BBMVs) were emulsified in a non-oil based adjuvant and used to immunize a group of ten Balb/c mice. Mice were given booster immunizations at biweekly intervals. Seven days following the third booster injection, serum samples were taken from the mice, and the relative serum antibody titers determined by an enzyme-linked immunosorbent assay (ELISA), as described below. A group of four mice with the highest titers were given a final regimen of low-dose antigen boosters (approximately one-tenth of the dosage used during the regular immunization) over a period of three days, and used as spleen donors in fusions as described below.

1.2. Fusion:

Four mice with specific antibody titers of >1:5,000 were selected for two fusions. Spleens were aseptically excised, mechanically dissociated and the lymphocytes isolated as follows. The red blood cells were lysed by incubation with a 0.155 M solution of ammonium chloride in 0.017 M TRIZMA base, pH 7.2 (Sigma Chemical Company, St. Louis, Mo.). The cells were washed twice with phosphate buffered saline (PBS) and lymphocytes further purified by running a density gradient centrifugation as follows. Cells were carefully layered on a Ficoll (Sigma Chemical Company, St. Louis, Mo.) solution of specific gravity 1.065 (Van Mourik et al., Meth. in Enzymology, 121:174–182 (1986)) and centrifuged at 450×g for 20 minutes. The pellet that contains cells of density greater than 1.065 is greatly enriched in lymphocytes, and was fused with myeloma cells.

A polyethylene glycol-mediated fusion was performed using isolated lymphocytes and a Balb/c-derived HGPRT (Hypoxanthine Guanine Phosphoribosyl Transferase) deficient SP2/0 plasmacytoma cell line. Lymphocytes were mixed with myeloma cells at a ratio of 4:1. The cell mixture was thoroughly mixed, centrifuged and the fusion carried out as follows (Oi et al. in Selected Methods in Cellular Immunology eds. Michell, B. B. and Shiigi, S. M. (Freeman, San Francisco) 351–371 (1980), Fazekas et al., J. Immunol. Meth., 35:1–21 (1980)). The cell pellet was carefully suspended in 1 ml of a 50% polyethylene glycol (PEG) with constant stirring over a period of one minute. The PEG concentration was gradually reduced by diluting the cells with serum free RPMI media (Gibco BRL, Gaithersburg, Md.). After the fusion, the fused cells were pelleted at 80×g for 5 minutes, resuspended and plated into 96 well plates at a density of $10^5$ to $10^6$ total cells per well. Spleen feeder cells, prepared by treating non-immune splenocytes with 20 μg/ml mitomycin C were added to provide supplemental growth factors to the fused cells. For the next several days, the hybridomas were selected by using HAT (Hypoxanthine Aminopterin Thymidine) media that contained 17.6 μg/ml of aminopterin. Growing colonies were seen under an inverted microscope as early as 3 or 4 days after fusion. However, macroscopic colonies were not visible until 10 to 14 days after fusion. At this stage, the supernatants of each well were assayed for specific antibody secretion.

1.3. Screening:

Upon detection of viable hybridoma colonies surviving HAT selection, the supernatants were screened using an enzyme-linked immunosorbent assay (ELISA) (Engvall, Meth. Enzymology, 70:419 (1980), Engvall et al., Immunochemistry, 8:871 (1971)). Very briefly, hybridoma supernatants were incubated in wells of 96-well microtiter plates bearing approximately 500 nanograms per well of the antigen. After appropriate washing steps, as described in Engvall et al. reference, bound antibodies were identified using a goat anti-mouse second antibody conjugated to horseradish peroxidase (HRP). After additional washing steps, the enzyme activity in each well was quantified with chromogenic substrate. The resultant absorbance at 492 nm (OD492) was measured with an automated ELISA reader to identify the positive colonies. Hybridoma lines with strong binding to the corn rootworm BBMVs were further screened by three additional ELISA screens to eliminate those monoclonals which bind to either mammalian or plant proteins. More specifically, ELISAs were performed using rabbit intestinal brush border membranes and maize leaf and root microsomal membrane preparations. An ELISA screen to identify lines with cross-reactivity to European corn borer BBMVs was also included.

Hybridoma colonies which secreted antibodies which bound to the corn rootworm BBMV antigen and not to the mammalian and plant proteins were cloned as described below.

1.4. Cloning:

In this phase, hybridomas which secrete antibodies with apparent specificity for the antigen were expanded and cloned in 96 well plates at target concentrations of 0.5, 1 and 5 cells/well. Growth factors (Sugasawara et al., J. Immunol. Meth., 79:276–275 (1985)) were provided to promote hybridoma cells grown from limited densities. After 2–3 weeks, when the clones were large enough, positive clones were identified again using the ELISAs as described under "Screening." Representative clones were then expanded for antibody production.

1.5. Ascites Production:

Large-scale production of appropriate monoclonal antibodies was accomplished by growing the hybridomas as ascites tumors in pristane-primed Balb/c mice (Brodeur et al., J. Immunol. Meth., 71:265–272 (1984)). Ascites fluid was pooled, and the antibodies partially purified from dialyzed ascites by Protein A chromatography. The resultant antibody preparations were aliquoted and frozen.

Cell lines which produce monoclonal antibodies useful in the present invention are described in Table 1. The hybridoma cell lines whose ATCC designations are indicated in Table 1 were deposited with the American Type Culture Collection 10801 University Blvd., Manassas, Va. 20110-2200, USA on Apr. 19, 1994, except hybridoma cell line 14G1, which was deposited Jun. 8, 1995.

TABLE 1

CRW BBMV MONOCLONAL LINES

| Cell line | ECB Crossreact | Western Blot | Isotype | ATCC Designation |
|---|---|---|---|---|
| 1A4 | yes | 2 CRW bands | IgM-k | |
| 1A11 | no | 2 CRW bands | IgM-k | |
| 1F51 | yes | 2 CRW bands | IgM-k | |
| 2B5 | yes | 2 CRW bands | IgM-k | HB 11619 |
| 3B1 | no | I CRW band | IgGI-k | HB 11617 |
| 7G6 | no | >5 bands | IgM-k | |
| 10A1 | no | no signal | IgM-k | |
| 10B6 | no | >5 bands C | IgG3-K | HB 11618 |
| 10F9 | no | >5 bands B | IgM-k | |
| 12G4 | no | not done | IgM-k | |
| 14G1 | no | >5 bands | IgG2B-k | HB 11936 |
| 17F6 | no | >5 bands A | IgG1-k | HB 11620 |
| 17H6 | no | >5 bands A | IgG2A-k | |
| 18A7 | no | >5 bands B | IgG1-k | |
| 16E4 | yes | >5 bands | IgM | HB 11616 |

EXAMPLE 2

Isolation of Brush Border Membranes Vesicles (BBMV)

2.1. Isolation of Corn Rootworm BBMV:

Vesicles were prepared based on the method of Wolfersberger et al., Comp. Biochem. Physiol. 86A:301–308 (1987) as modified by English and Readdy (Insect Biochem. 19;145–152 (1989)). The guts of third instar corn rootworm larvae were homogenized in ice-cold 50 mM sucrose, 2 mM Tris-Cl (pH 7.4), 0.1 mM phenylmethylsulfonyl fluoride using a Potter-Elvenhem homogenizer. Calcium chloride was added to 10 mM and the homogenate stirred on ice for 15 min. The homogenate was centrifuged at 4,300×g for 10 min at 4° C., and the pellet discarded. The supernatant was centrifuged at 27,000×g for 10 min, and the pellet resuspended in 0.32 M sucrose. The suspension was passed through a 27-gauge needle and stored at −70° C.

2.2. Isolation of European Cornborer BBMV:

Guts were excised from fifth instar European corn borer (ECB) and cut longitudinally to remove the food contents and peritrophic membrane. Isolation of (ECB) BBMVs were performed using the methods described above.

2.3. Isolation of Plant Microsomes:

Leaf or root tissue from corn plants (grown 72 hrs in dark at 28° C.) were ground up with a mortar and pestle in an equal volume of 0.3 M potassium phosphate pH 7.4, 5 mM DTT, and 1% (w/v) PVPP. The mixture was strained through four layers of cheesecloth, followed by centrifugation at 10,000×g for 15 min. The supernatant was centrifuged at 100,000×g for 60 min and the pellet resuspended in 0.1 M potassium phosphate pH 7.4.

2.4. Isolation of Mammalian Intestinal BBMV:

Mammalian brush border membranes were prepared from the mucosal surface of rabbit duodenum and stroma (Kessler et al. BBA 506:136–154 (1978)) using a similar process to the isolation of brush border membrane vesicles from insect guts. The mucosal lining of fresh rabbit duodenum and lower stomach was washed and the mucosal layer separated from the underlying stroma. The material was suspended in a 10-fold volume of ice-cold 50 mM sucrose, 0.1 mM PMSF, 2 mM Tris-HCl (pH7.4) and homogenized with 15 strokes on ice. Calcium chloride was added to a final concentration of 10 mM, and the mixture stirred on ice for 15 min. The homogenate was centrifuged at 4300×g for 10 min at 4° C. The supernatant was harvested and centrifuged at 27,000×g for 10 min. The pellet was resuspended in 0.32 M sucrose and frozen at −70° C.

EXAMPLE 3

Characterization of CRW BBMV Monoclonal Lines

Monoclonal lines with strong binding to CRW BBMVs based on ELISA were further screened to select clones with no cross-reactivity to either maize or mammalian microsomes. The additional ELISAs were performed using corn leaf and root microsomes and rabbit intestinal membrane vesicles. All lines were simultaneously screened against European corn borer BBMV proteins. From seventy-eight lines screened, eleven specific to corn rootworm were isolated. In addition to the eleven CRW BBMV-specific lines, four lines with cross-reactivity to ECB BBMVs were isolated. The fifteen lines represent monoclonal lines secreting IgG1, Ig2a, IgG2b, IgG3 and IgM. Monoclonal lines were analyzed by western blot to confirm CRW specificity and absence of cross-reactivity to either rabbit or corn microsomes. The specific binding of the antibodies to various CRW BBMV proteins was also characterized and shown in FIG. 1. Five distinct binding patterns were found; two patterns were specific for one or two proteins and the other three represent binding to 7–15 proteins. The class with 7–15 proteins was further subclassed into A, B, C based on binding pattern.

3.1. Western Analysis of Monoclonal Lines:

Brush border membrane vesicles were prepared as described above and electrophoresed on 8–16 % acrylamide SDS protein gels (Novex, San Diego, Calif.). Proteins were transferred onto nitrocellulose, (Burnette, W. N., Western Blotting, 112:195 (1981)) and allowed to bind the supernatant of hybridoma lines. Binding of antibodies to blotted proteins was visualized using standard methods (see, for example, Antibodies: A Laboratory Manual, E. Harlow and D. Lane, Cold Spring Harbor, 1988, and references cited therein).

EXAMPLE 4

Cloning CRW Binding Antibody Domains

Various methods are known for obtaining corn rootworm specific antibody genes. One method is to clone a random library of antibody genes in a phage and screen the library for ability to bind to corn rootworm gut (CRW) proteins. Another available approach is to generate monoclonal antibodies which bind to CRW gut proteins and then clone the antibody genes from such lines. For the present example, the second method is used. Antibody genes can be cloned from hybridoma cells using primers to conserved DNA sequences within the constant regions and the framework regions of the variable regions and amplified for cloning using the polymerase chain reaction (PCR). See generally, Mullis etal., Meth. Enzymol., 155:335–350 (1987); Erlich, (ed.), PCR Technology, Stockton Press (New York 1989). A database of mouse heavy chain and light chain sequences compiled by Kabat et al., US Dept Health and Human Services, US Government Printing Offices (1987) has been successfully used to generate both isotype specific and degenerate primers for cloning antibody genes. (Jones et al. Bio/technology 9:88–89 (1991)). Additionally, techniques are well known for cloning of smaller fragments of antibodies (Fab) which possess the binding properties of the original antibody. Complete antibodies are large molecules (150 kDa), but much smaller Fab and Fv antigen-binding fragments (12 kDa–50 kDa) have been shown to retain full binding affinity. Single chain Fv fragments (scFv) in which Vh and Vl domains are linked by a hydrophilic and flexible peptide have been used successfully to target enzymes and toxins to specific cells (Bird, Science 423:423–426 (1988); Huston, PNAS 85:5879–5883 (1988)). Single Vh domains (Dabs) and single complementary determining regions as small as 20 amino acids in length, called minimal recognition units (m.r.u.), have also been used for antigen binding (Ward, Nature 341:544–546 (1989); Taub, J. Biol. Chem 264:259–265 (1989); Williams, PNAS 86:5537–5541 (1989)). Thus, it is possible to reduce the CRW specific binding domain to a very small size.

4.1. Cloning Antibody Genes by PCR:

Polymerase chain reaction technology and specific oligonucleotide primers were used to clone immunoglobulin genes or regions from immunoglobin genes. PCR primers specific for both the heavy and light chains of IgM and the three IgG isotypes were selected from the Kabat database described above. Primers for the region encoding the $NH_2$-terminal end of the mature variable region were designed to initiate at the first framework region and were made with some degeneracy to allow these to be used as "universal primers". The 3' primers used for the specific PCR amplification of the variable regions were designed from conserved sequences of the first constant domain (CH1) of both the light and heavy chains. A different 3' primer was used for immunoglobulin isotypes IgG1 (3B1 and 17F6), IgG3 (10B6), and IgM (2B5). Isotypes IgG2A and IgG2B can be amplified with the same primers used for IgG1. Antibody variable regions were cloned into a light (pCIB4612) and heavy (pCIB461 1) chain expression vector containing an endoplasmic reticulum signal peptide and the constant regions of IgG1 light and heavy chains, respectively.

Table 2 shows the structure of the primers used for the PCR cloning of the mouse immunoglobulin light and heavy variable regions. Alternatively, primer sequences can be used that are available in the published literature (Coloma et al. Bio/Techniques 11: 152–156, 1991; Jones et al. Bio/Technology 9:88–89, 1991). Oligonucleotides were made on an Applied Biosystems DNA synthesizer 380B (Applied Biosystems, Foster City, Calif.) using standard conditions as described below. The PCR primers incorporate restriction sites and, after amplification and digestion, were cloned into a plant expression vector under the control of the CaMV 35S promoter. Restriction sites were chosen that were known to be absent in sequenced antibody genes.

TABLE 2

| PCR PRIMERS USED FOR AMPLIFICATION OF ANTIBODY GENES |
|---|
| 3B1, 2B5, 10B6, 14G1 and 17F6 Light Chain Variable Regions in pCIB4614, pCIB4616, pCIB4625, DCIB4636 and DCIB4617: |
| NC92: 5'Primer 5'-GTC TCG AGG AYA TYS WGM TSA CCC ART CT-3' (SEQ ID NO:37) |
| NC130: 3'Primer 5'-GCA GAT CTA GTT GGT GCA GCA TCA GCC CG-3' (SEQ ID NO:38) |
| 3B1 and 17F6 Heavy Chain Variable Region in pCIB4613 and pCIB4609: |
| NC91: 5'Primer 5'-GTC TCG AGC AGG TSM ARC TGC AGS AGT CWG-3' (SEQ ID NO:39) |
| NC114: 3'Primer 5'-GCA GAT CTA GAT CCA GGG GCC AGT GGA TA-3' (SEQ ID NO:40) |

TABLE 2-continued

| PCR PRIMERS USED FOR AMPLIFICATION OF ANTIBODY GENES |
|---|
| 2B5 Heavy Chain Variable Region in pCIB4615: |
| NC91: 5'Primer 5'-GTC TCG AGC AGG TSM ARC TGC AGS AGT CWG-3' (SEQ ID NO:39) |
| NC111: 3'Primer 5'-GCA GAT CTG CAG GAG ACG AGG GGG MG ACA TT-3' (SEQ ID NO:41) |
| 10B6 Heavy Chain Variable Region in pCIB4637: |
| DB91: 5'Primer 5'-ACG TCT CGA GGA RGT GAA GCT KRW KGA RWC TG-3' (SEQ ID NO:48) |
| NC117: 3'Primer 5'-GCA GAT CTG CAG CCA GGG ACC AAG GGA TA-3' (SEQ ID NO:42) |
| 14G1 Heavy Chain Variable Region in pCIB4635: |
| DB91: 5'Primer 5'-ACG TCT CGA GGA RGT GM GCT KRW KGA RWC TG-3' (SEQ ID NO:48) |
| DB114: 3'Primer 5'-CAA TTC GCA TAT GAG ATC CAG GGG CCA GTG GAT A-3' (SEQ ID NO:49) |

Y = C or T; S = C or G; W = A or T; M = C or A; R = A or G

Poly-A+ RNA isolated from hybridoma lines was used to generate first strand cDNA for subsequent use in PCR reactions. Poly-A+ RNA was extracted from $10^8$ hybridoma cells using a procedure based on guanidinium thiocyanate lysis and oligo (dT) cellulose purification using the Fast Track mRNA Isolation Kit, (Invitrogen Corp., San Diego, Calif.). Approximately one tenth of the RNA isolated from $10^8$ cells (or ~500 ng) was used to generate first strand cDNA. RNA was incubated at 42° C. for 30 min then heated to 95° C. for 5 min with a mixture of deoxynucleotides (0.2 mM each dNTP), 5 μg random hexamer pd (N6) (Pharmacia LKB Biotechnology Inc., Piscataway, N.J.) as primer, 50 units Moloney Murine Leukemia Virus reverse transcriptase (Pharmacia LKB Biotechnology Inc., Piscataway, N.J.) and 1×PCR buffer in a 100 μl reaction volume. The first-strand cDNA reaction was extracted with phenol-chloroform and centrifuged through a size exclusion spin column (Chroma Spin 30, Clontech Laboratories, Inc., Palo Alto, Calif.) to remove random hexamers. Next, one tenth (or 10 μl) of the first-strand cDNA reaction was added to a 50 μl PCR reaction mix containing immunoglobulin specific primers following the instructions of the Perkin-Elmer Cetus Amplification Kit. The mixture was amplified using the Perkin-Elmer Cetus Thermal Cycler for 20 cycles. The temperature and times used for PCR were as follows: denaturation at 94 C for 1 min; annealing at 52 C for 1 min 30 sec; extension at 72 C for 1 min. PCR products were electrophoresed on 6% acrylamide gels (Novex, Encinitas, Calif.) and DNA purified from gel slices. Gel slices were crushed in 200 μl TE and purified by centrifugation through Ultrafree-MC Millipore columns (Millipore, Bedford, Mass.). Eluate was treated with 50 μg/ml proteinase K at 37 C for 30 min, extracted with phenol-chloroform-isoamyl (50:48:2), followed by an additional chloroform extraction and ethanol precipitated. DNA was resuspended in 40 μl TE and digested with appropriate restriction enzymes. PCR products of antibody variable regions were digested with Xho I and Bgl II and re-purified on 6% acrylamide gels as described above. Final Xho I/Bgl II fragments were ligated to either the light (pCIB4612) or the heavy (pCIB4611) antibody chain expression vector digested with Xho I and Bgl II. Expression vector pCIB4612 contains the CaMV 35S promoter and termination sequence with a 19 amino acid signal peptide sequence and the light chain constant region CH1. Variable light chain regions were cloned into the Xho I/Bgl II site for expression of a full length light chain.

All antibody genes were cloned by the above procedure except the heavy chain of 10B6 and the heavy and light chains of 14G1. These antibody genes were cloned from PCR products, but the products were separated by electrophoresis on 6% acrylamide TBE gels, the fragments cut out of the gel and eluted into 0.7 M LiCl plus 2 mM EDTA. The fragments were precipitated and resuspended in 10 mM Tris plus 2 mM EDTA, pH 7.5. The isolated PCR products were ligated directly into a pUC derived cloning vector, pT&Blue T (Novagen, Inc.). Since Taq DNA polymerase leaves a single 3' A-nucleotide overhang on the reaction products (Clark, Nucl. Acids Res. 16: 9677 (1988)), these products can be cloned directly into a vector containing compatible single T-nucleotide overhangs (Marchuk et al. Nucl. Acids Res. 19: 1154 (1990)).

The pCIB4612 vector was made by ligating a 155 base pair Dde I/Sty I light chain constant region from a mouse Ig Kappa chain (Schulze-Gahmen et al. 1988, J. Biol. Chem. 263;17100–17106; Kabat etal., US Dept Health and Human Services, US Government Printing Offices (1987)) in a four way ligation to a 71 bp Xho I/Dde I fragment, a 101 bp Sty I/Bgl II fragment, and a 3.8 Kb Xho I/Bgl II vector fragment from pCIB4610. Oligonucleotides KE109A28 and KE110A28 were hybridized to make the 101 bp fragment with StyI and Bam HI staggered ends.

KE109A28: 5'-CAA GGA CGA GTA TGA ACG ACA TAA CAG CTA TAC CTG TGA GGC CAC TCA CAA GAC ATC AAC TTC ACC CAT TGT CAA GAG CTT CAA CAG GAA TGA GTG TTA GG-3' (SEQ ID NO: 19)

KE110A28: 5'-GAT CCC TAA CAC TCA TTC CTG TTG AAG CTC TTG ACA ATG GGT GAA GTT GAT GTC TTG TGA GTG GCC TCA CAG GTA TAG CTG TTA TGT CGT TCA TAC TCG TC-3' (SEQ ID NO: 20)

Oligonucleotides KE111A28 and KE112A28 were hybridized to make the 71 bp fragment with Xho I and Dde I staggered ends.

KE111A28: 5'-TCG AGG GTA CCG AGC TCT AGA TCT GTA TCC ATC TTC CCA CCA TCC AGT GAG CAG TTA ACA TCT GGA GGT GCC-3' (SEQ ID NO: 21)

KE112A28: 5'-TGA GGC ACC TCC AGA TGT TAA CTG CTC ACT GGA TGG TGG GAA GAT GGA TAC AGA TCT AGA GCT CGG TAC CC-3' (SEQ ID NO: 22)

Expression vector pCIB4611 contains heavy chain constant regions CH1–CH3, and likewise variable heavy chain regions can be cloned into the Xho I/Bgl II site for expression of a full length heavy chain. The pCIB4611 vector was made by ligating a Nco I/Bst XI 902 bp heavy chain constant region from a mouse IgGG1 Gamma chain (Honjo, et al. 1979, Nature 277:627–633; Kabat et al., US Dept Health and Human Services, US Government Printing Offices (1987)) with two 40 bp hybridized oligonucleotide fragments and ligating the final 982 bp fragment into pCIB4610 digested with Bgl II and Xho I. One 40 bp fragment was hybridized from oligos KE106A28 and KE107A28 and has Xho I/Nco I staggered ends and the other 40 bp fragment was hybridized from KE108A28 and KE105A28 and has Bst XI/Bam HI staggered ends.

KE106A28: 5'-TCG AGG GTA CCG AGC TCT AGA TCT GCT GCC CAA ACT AAC TC-3' (SEQ ID NO: 23)

KE107A28: 5'-CAT GGA GTT AGT TTG GGC AGC AGA TCT AGA GCT CGG TAC CC-3' (SEQ ID NO: 24)

KE108A28: 5'-CTG GTA AAG GCG GCC GCA TCG ATT AAG TCG ACC CGC GGG-3' (SEQ ID NO: 25)

KE105A28: 5'-GAT CCC CGC GGG TCG ACT TAA TCG ATG CGG CCG CCT TTA CCA GGA GA-3' (SEQ ID NO: 26)

The pCIB4610 vector contains a 19 amino acid mouse endoplasmic reticulum signal peptide sequence between CaMV 35S promoter and CaMV 35S termination sequences. The pCIB4610 vector was made by ligating pCIB4600 digested with Bam HI and Hpa I to a 83 bp PCR generated fragment digested with Bam HI and Hpa I. The POR generated fragment was made using pCIB4600 as a template and PCR primers KE102A28 and KE101A28. PCIB4610 differs from pCIB4600 only in the untranslated leader region following the CaMV 35S promoter. pCIB4610 contains a plant consensus translational initiation sequence AACA ATG (SEQ ID NO: 27) where ATG is the start of translation, and pCIB4600 contains the sequence TCCG ATG (SEQ ID NO: 28).

KE102A28: 5'-CGA AGT TAA CAG ATC TAG AGC TCG G-3' (SEQ ID NO: 29)

KE101A28: 5'-CGG GAT CCA ACA ATG GGA TGG AGC TGG ATC TT-3' (SEQ ID NO: 30)

The pCIB4600 vector was made by ligating a derivative of the CaMV 35S expression vector pCIB710 (Rothstein, et al. (1987) Gene 53:153–161) digested with Bam HI and Sac I with a 86 bp Bam HI and Sac I fragment encoding an endoplasmic reticulum signal peptide (Kabat et al., US Dept Health and Human Services, US Government Printing Offices (1987)). The 86 bp fragment contains the following sequence:

5'-GAT CCA ACA ATG GGA TGG AGC TGG ATC TTT CTC TTC CTC CTG TCA GTT GTT ACC CTA CCT CGA CCT AGA AAG AGA AGG AGG ACA GTG GAG CTG CAG GTG TCC ATT GCC TAC TCG AGG GTA CCG AGC TCC TCG ACG TCC ACA GGT AAC GGA TGA GCT CCG ATG GC-3' (SEQ ID NO: 31)

Variable light and heavy chain regions were cloned from five CRW monoclonal lines into the expression vectors to generate the following constructs:

pCIB4613: 3B1 heavy chain variable region pCIB4614: 3B1 light chain variable region pCIB4615: 2B5 heavy chain variable region (NRRL B-21216)

pCIB4616: 2B5 light chain variable region (NRRL B-21217)

pCIB4609: 17F6 heavy chain variable region (NRRL B-21215)

pCIB4617: 17F6 light chain variable region (NRRL B-21218)

pCIB4637: 10B6 heavy chain variable region (NRRL B-21279)

pCIB4625: 10B6 light chain variable region (NRRL B-21219)

pCIB4635: 14G1 heavy chain variable region (NRRL B-21277)

pCIB4636: 14G1 light chain variable region (NRRL B-21278)

pCIB4631: 3B1 light and heavy chain variable region (NRRL B-21220)

The expression vectors listed above that are followed by an NRRL accession number were deposited on Mar. 7, 1994 with Agricultural Research Service, Patent Culture Collection (NRRL), Northern Regional Research Center, 1815 North University Street, Peoria, Ill. 61604, U.S.A., with the exception of pCIB4637, pCIB4635 and pCIB4636, which were deposited on Jun. 3, 1994.

Table 3 contains a listing of the sequence ID numbers for the variable region sequences. The sequence in the cases of pCIB4613, pCIB4617, pCIB4625, pCIB4637, pCIB4635 and pCIB4636 are complete variable regions starting at the first codon of the first framework region and ending with the last codon of the fourth framework region of the variable region. The variable region in pCIB4609 is not complete, the 5' end of the coding sequence is truncated and the sequence begins in the second CDR region of the variable region.

TABLE 3

LIST OF ANTIBODY CHAIN DNA SEQUENCES

| SEQ ID NO:1 | 3B1 Heavy chain variable region DNA |
| SEQ ID NO:2 | 3B1 Heavy chain variable region protein |
| SEQ ID NO:3 | 3B1 Light chain variable region DNA |
| SEQ ID NO:4 | 3B1 Light chain variable region protein |
| SEQ ID NO:5 | 2B5 Heavy chain variable region DNA |
| SEQ ID NO:6 | 2B5 Heavy chain variable region protein |
| SEQ ID NO:7 | 2B5 Light chain variable region DNA |
| SEQ ID NO:8 | 2B5 Light chain variable region protein |
| SEQ ID NO:9 | 17F6 Heavy chain variable region DNA |
| SEQ ID NO:10 | 17F6 Heavy chain variable region protein |
| SEQ ID NO:11 | 17F6 Light chain variable region DNA |
| SEQ ID NO:12 | 17F6 Light chain variable region protein |
| SEQ ID NO:13 | 10B6 Heavy chain variable region DNA |
| SEQ ID NO:14 | 10B6 Heavy chain variable region protein |
| SEQ ID NO:15 | 10B6 Light chain variable region DNA |
| SEQ ID NO:16 | 10B6 Light chain variable region protein |
| SEQ ID NO:17 | 3B1 single chain antibody DNA |
| SEQ ID NO:18 | 3B1 single chain antibody protein |
| SEQ ID NO:44 | 14G1 Heavy chain variable region DNA |
| SEQ ID NO:45 | 14G1 Heavy chain variable region protein |
| SEQ ID NO:46 | 14G1 Light chain variable region DNA |
| SEQ ID NO:47 | 14G1 Light chain variable region protein |

4.2. Synthesis of DNA Oligomers:

DNA oligomers were synthesized using an Applied Biosystems model 380B DNA synthesizer and standard procedures. The oligomers were made using the updated SSCAF3 cycle on a 0.2 μmole, wide pore, small scale ABI column. The end procedure was run trityl off and the oligomer was cleaved from the column using the 380B's automatic cleavage cycle. The oligomers were then deblocked in excess ammonium hydroxide ($NH_4OH$) at 55 C for 8–12 hours. The oligomers were then dried in an evaporator using nitrogen gas. After completion, the oligomers were resuspended in 0.25–0.5 ml of deionized water.

4.3. Purification of Synthetic DNA Oligomers:

An aliquot of each oligomer was mixed wit h an equal volume of blue dye/formamide mix with the final solution containing 0.05% bromophenol blue, 0.05% xylene cyanol FF, and 25% formamide. This mixture was heated at 95 C for 10 minutes to denature the oligomers. Samples were th en applied to a 12% polyacrylamide-urea gel containing 7 M urea (Sambrook et al.). After electrophoresis at 300–400 volts for 3–4 hours using a Vertical Slab Gel Unit (Hoefer Scientific Instruments, San Francisco, Calif.), UV shadowing was used to locate the correct sized fragment in the gel which was then excised using a razor blade. The purified gel fragment was minced and incubated in 0.4 M LiCl, 1 mM EDTA (pH 8) buffer overnight at 37 C.

Either of two methods was then used to separate the oligomers from the polyacrylamide gel remnants: Gel/X (Genex Corp., Gaithersburg) micron porous polyethylene filter units or Millipore's ultrafree-MC 0.45 micron filter units. The purified oligomers were ethanol precipitated, recovered by centrifuging in a microfuge for 20 min at 4 C, and finally resuspended in TE (10 mM Tris, 1 mM EDTA, pH 8.0). Concentrations were adjusted to 50 ng/μl based on absorption readings at 260 nm.

4.4. Kinasing Oligomers:

In each 20 μl kinase reaction, one picomole of purified oligomer was used in a buffer of 7.0 mM Tris pH 7.5, 10 mM KCl, 1 mM $MgCl_2$), 0.5 mM DTT, 50 μg/ml BSA, 3000 μCi (3 picomoles) of $^{32}P$-γ-ATP, and 8 units of T4 polynucleotide kinase. The kinase reaction was incubated for 1 hour at 37 C, followed by a phenol/chloroform extraction and three ethanol precipitations with glycogen as carrier (Tracy, Prep. Biochem. 11:251–268 (1981)).

4.5.Hybridizing Oligomers for Direct Cloning:

Oligomers to be hybridized were pooled together (from 1 μg to 20 9g total DNA) and kinased at 37 C for 1 hour in 1×Promega ligation buffer containing 30 mM Tris-HCl pH 7.8, 10 mM $MgCl_2$, 10 mM DTT, and 1 mM dATP. One to 20 units of T4 polynucleotide kinase was used in the reaction, depending on the amount of total DNA present. The kinasing reactions were stopped by placing the reaction in a boiling water bath for five minutes. The pooled oligomers were in a volume of 50–100 μl with added hybridization buffer used to adjust the final salt conditions to 100 mM NaCl, 120 mM Tris pH 7.5, and 10 mM $MgCl_2$. The kinased and non-kinased oligomers were pooled together and heated in a boiling water bath for five minutes and allowed to slowly cool to room temperature over a period of about four hours. The hybridized oligomers were then phenol/chloroform extracted, ethanol precipitated, and resuspended in 17 l of TE (10 mM Tris, 1 mM EDTA, pH 8.0). Using this 17 l, a ligation reaction with a final volume of 20 l is assembled (final conditions=30 mM Tris-HCl pH 7.8, 10 mM $MgCl_2$, 10 mM DTT, 1 mM ATP, and 3 units of T4 DNA ligase (Promega, Madison Wis.). The ligation was allowed to incubate for about 2 hours at room temperature. The hybridized/ligated fragments were generally purified on 2% Nusieve agarose (FMC BioProducts, Rockland, Me.) gels before and/or after cutting with restriction enzymes and prior to cloning into vectors. A 20 l volume ligation reaction is assembled using 100 ng to 500 ng of each fragment with approximate equimolar amounts of DNA in 30 mM Tris-HCl pH 7.8, 10 mM $MgCl_2$, 10 mM DTT, 1 mM ATP, and 3 units of T4 DNA ligase (Promega; Madison, Wis.). Ligations were incubated at room temperature for 2 hours. After ligation, DNA was transformed into frozen competent *E. coli* cells using standard procedures (Sambrook et al.) and transformants were selected on LB-agar (Sambrook et al.) containing 100 μg/ml ampicillin (see below).

EXAMPLE 5

Construction of a Single Chain Antibody (SCA) Molecule pCIB4631 contains a single chain antibody (SCA) specific to CRW BBMVs fused to the constant regions of the antibody heavy chain gene. The SCA gene contains the fusion of variable fragments from antibody 3B1 light and heavy chains, (from monoclonal antibody line 3B1 specific to CRW BBMV) with a 19 amino acid endoplasmic reticulum signal sequence. Between the light and heavy Fv fragments is a 10 amino acid (GGGGSGGGGS; SEQ ID NO: 32) domain linker (Huston et al., PNAS 85:5879–5883 (1988). pCIB4631 was made by ligating a 4.1 Kb Xba I/Xho I fragment (Fv: constant heavy chain: CaMV 35S termination region: vector fragment from pCIB4613) and a 1.4 Kb Xba I/Bgl II fragment (CaMV 35S promoter: light Fv fragment from pCIB4614), and a hybridized 36 base pair linker fragment with Bgl II/Xho I staggered restriction enzyme site ends.

Oligos KE147A28 and KE182A28 were hybridized together in making a 36 base pair linker:

KE147A28: 5'-GAT CTG GTG GCG GTG GCT CGG GCG GTG GTG GGT CGC-3' (SEQ ID NO: 33)

KE182A28: 5'-TCG AGC GAC CCA CCA CCG CCC GAG CCA CCG CCA CCA-3' (SEQ ID NO: 34)

Oligomers were purified as described above on a 12% polyacrylamide/7M urea gel using UV shadowing to cut-out the correct size oligomers using standard procedures. Oligos were kinased and hybridized as described above.

Expression vector pCIB4631 was deposited on Mar. 7, 1994 with the Agricultural Research Service, Patent Culture Collection (NRRL), Northern Regional Research Center, 1815 North University Street, Peoria, Ill. 61604, U.S.A. and was assigned accession number NRRL B-21220.

EXAMPLE 6

Characterization of SCA Binding Properties

Single chain antibody proteins were expressed in maize protoplasts, isolated, and shown to bind CRW BBMV proteins on both a western blot and isolated cross-sections of CRW midguts in immunosections (Bravo et al. 1992, J. of Invert. Path. 60:237–246, Bravo et al 1 992, J. of Invert. Path. 60:247–253).

6.1. Isolation of Maize Suspension Cell Protoplasts:

Embryogenic suspension cultures derived from immature embryo cultures of a Ciba Seeds maize inbred (B73 type) or alternatively Black Mexican Sweet were maintained in N6 basal medium (Chu etal., 1975) supplemented with 3% sucrose and 2 mg/l 2, 4-D, at 27 C on a gyratory shaker at 130 rpm and sub-cultured weekly. Suspension cells were collected 1–2 days after subculturing and resuspended in enzyme solution (3% cellulase RS+1% macerozyme R10 dissolved in KMC: 8.7 g/l KCl, 12.5 g/l $CaCl_2$, 16.4 g/l $MgSO_4$, 5 g/l MES, pH 5.7) at a ratio of 2 ml packed cell volume per 20 ml enzyme solution. Cells were aliquoted in to 100×25 mm Petri dishes and incubated for four hours at room temperature on a gyratory shaker at 50 rpm.

6.2. Transformation of Protoplasts:

Immediately after isolation, protoplasts were resuspended at a density of 6 million/ml in RS buffer (0.45 M mannitol, 15 mM $CaCl_2$, 0.1 % MES, pH 5.7). One-half ml aliquots were placed in 17×100 mm polystyrene tubes, followed by 50 μg pCIB4631 DNA and 50 μg CaMV 35S GUS such as pB1221 from Clontech Laboratories, Inc., Palo Alto, Calif., as tranformational control. One-half ml of PEG solution (40% PEG 6000, 0.4 M mannitol, 0.1 M $Ca(NO_3)_2$ was added to each tube and mixed with protoplasts by gentle shaking. After a 30 mM incubation at room temperature, protoplasts were diluted stepwise at 5 minute intervals with 1 ml, 2 ml, 5 ml, and 1 0 ml W5 (9.0 g/l NaCl, 18.5 g/l $CaCl_2$, 0.37 g/l KCl, 0.9 g/l glucose pH 5.6), sedimented, and resuspended in plating medium (MS salts, B5 vitamins, 3% sucrose, 2 mg/l 2,4-D, 0.3M mannitol) at a density of $2×10^6$ protoplasts/ml. Protoplasts were incubated in the dark at 26 C. At 18–22 hrs, protoplasts were collected in Eppendorf tubes, sedimented, and resuspended in 0.4 ml extraction buffer (100 mM $KHPO_4$ pH 7.8, 1 mM DTT). Samples were then sonicated for 10 seconds and debris pelleted by centrifugation.

6.3. Single Chain Antibody Binding to CRW BBMV:

Brush border membrane vesicles were prepared as described above and electrophoresed on 8–16% acrylamide SDS protein gels (Novex, San Diego, Calif.). Proteins were transferred onto nitrocellulose (Burnette, W. N., Western Blotting, 112:195 (1981) and allowed to bind maize protoplast extracts containing the single chain antibody protein. The CRW BBMV-specific 3B1 single chain antibody protein expressed from pCIB4631 bound the same molecular weight BBMV protein on the western blot as did the original 3B1 monoclonal. The single chain antibody expressed in maize protoplasts was also shown to bind to cross-sections of CRW midgut in immunosectioning experiments (Bravo et al. 1992, J. Invert. Path. 60:237–246, Bravo et al. 1992, J. Invert. Path. 60:247–253).

EXAMPLE 7

Construction of CRW Specific Immunotoxin

A CRW BBMV specific single chain antibody was fused to the toxic domain from Pseudomonas exotoxin A. Pseudomonas exotoxin A has been used to synthesize recombinant hybrid antibody-toxin fusion proteins for treatment of cancer and immunological diseases (Pastan, I. and FitzGerald, D., 1989, J. Biol. Chem. 264:15157–15160, and Pastan, I etal. Annu. Rev. Biochem. 1992 61:331–54). The structure of Pseudomonas exotoxin is well characterized and its mode of action known. The idea of antibody hybrid toxins as insecticidal agents is novel and there is no precedent for this type of approach.

Pseudomonas exotoxin (PE) is a single chain toxin secreted by *Pseudomonas aeruginosa*. It kills cells by catalyzing the irreversible ADP-ribosylation and inactivation of translational elongation factor 2 (EF-2). The structure of PE is well characterized (Chaudhary, V. K. etal., 1990, J. Biol. Chem. 265:16303–16310), and consists of three domains. Domain la is responsible for the cell recognition and binding of PE to target cells, domain II is required for the translocation of the ADP-ribosylating activity into the cytosol and domain III is the ADP-ribosylating activity. When the toxin enters the cell it is internalized by endocytic vesicles where cleavage occurs to generate a 37 kD domain III "activated toxin". Deletion of domain la removes the cell binding domain and generates a 40 kDa protein (PE40) with "extremely low" cellular cytotoxicity. The fusion of antibodies to PE40 has been used to make many recombinant immunotoxins for cancer therapy. It is believed that the binding of the antibody-PE40 fusion must be followed by internalization by receptor-mediated endocytosis for proper activation of the PE40 and subsequent passage to the cytosol.

The PE toxic domain was fused to the —COOH terminus of the heavy chain fragment of the CRW 3B1 single chain since it has been shown that fusions to the —NH2 terminus of PE40 retain cytotoxicity. It is also possible to design the fusions such that the single-chain antibody is fused to the —COOH terminus of PE40 (Prior et al. Cell Vol. 64:1017–1023). Single-chain antibody fusions were made and tested in *E. coli* expression vectors, using the p-FLAG expression vector which has an IPTG inducible tac promoter followed by sequences encoding the ompA signal peptide for secretion into the periplasm and the eight amino acid FLAG epitope which allows the isolation of recombinant protein by antibody affinity chromatography. Single chain antibody fusion proteins were purified from the FLAG expression vector. The purified SCA fusion proteins are incorporated into a corn rootworm insect diet for activity assays.

A single chain antibody fused to PE40 was made by ligating a ~1.2 Kb Sph I/Eco RI fragment containing PE40 and a 790 bp Hind III/Sph I fragment containing the 3B1 single chain antibody into the 5.37 Kb Hind III/Eco RI digested pFLAG vector (IBI, New Haven, Conn.). The PE40 fragment was obtained from pWW20, a vector containing the toxic domain of Pseudomonas exotoxin A under control of an inducible Lac promoter in a pUC9 vector (Wels et al. 1992, Cancer Research 52:6310–6317). The 700 bp fragment containing the 3B1 single chain antibody was generated by PCR using pCIB4631 as template and PCR oligos NC200 and NC202.

NC200: 5'-CGA AGC TTG ACA TTG TGC TGA CCC AG-3' (SEQ ID NO: 35)

NC202: 5'-GCC CTC TAG AAG CAT GCC TGA GGA GAC GGT GAC TGA-3' (SEQ ID NO: 36)

EXAMPLE 8

Transformation and Expression in Plants

Hybrid toxins comprised of antibody domains fused to toxin domains are transformed into plants using current methodology as set forth in WO 93/07278, 08/008,006, and 08/037,057. Binary toxins comprised of two independent antibody chains or antibody domains fused to toxins are expressed and assembled in plants using normal cellular processing. Single chain antibody-toxin proteins are either expressed in the plant cytoplasm, targeted to the plant apoplast, or in the case of hybrid toxins that have cellular toxicity, targeted to organelles within the plant cell (Taviadoraki et al. 1993, Nature 366:469–472; Owen et al. 1992, Bio/Technology 10: 790–794; Firek et al. 1993, Plant Molecular Biology 23: 861–870). Techniques known in the literature are used to target proteins to the chloroplast or the vacuole via the endoplasmic reticulum. Vacuolar targeting signals in the form of carboxyl-terminal propeptides are described in the literature (Bednarek S. et al. 1991, Plant Cell 3:1195–1206; Neuhaus J- M et al. 1991, PNAS 88:10362–10366; Bednarek S. et al. 1992, Plant Mol. Biol. 20:133–150; Chrispeels M. J. etal. 1992, Cell 68:613–616; Nakamura K. et al. 1993, Plant Physiol. 101:1 –5; Dombrowski J. E. et al. 1993, Plant Cell 5:587–596; Schroeder M. R. et al. 1993, Plant Physiol. 101:451–458). Chloroplast targeting signals in the form of N-terminal transit peptides are described in the literature (Van Den Broeck G. et al. 1985, Nature 313:358–363; Smeekens S. et al. 1987, Plant Mol. Biol. 9:377–388; Szabo L. J. et al. 1987, In *Plant DNA Infectious Agents,* eds. T. Hohn and J. Schell, Springer Verlag, Wein, N.Y., pp. 321–339; Keegstra K. etal. 1989, Annu. Rev. Plant Physiol. Plant Mol. Biol. 40:471–501).

The present invention provides material and methods for the construction of toxin molecules which are targeted to a particular insect. Insects which have evaded toxin binding and cytotoxic effects of Bt endotoxins are specifically targeted. Furthermore, the toxin molecules are constructed so that they are specific to the particular insect pest.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the claims.

EXAMPLE 9

Formulation Examples

The active ingredient used in following formulation examples are the purified SCA fusion proteins prepared according to Example 7.

| A1. Wettable powders | a) | b) | c) |
|---|---|---|---|
| Active ingredient | 25% | 50% | 75% |
| sodium lignosufonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxid) | — | 2% | — |
| highly dispersed silicid acid | 5% | 10% | 10% |
| kaolin | 62% | 27% | — |

The spores are thoroughly mixed with the adjuvants and the mixture is thoroughly ground in a suitable mill, affording wettable powders which can be diluted with water to give suspensions of the desired concentrations.

| A2. Emulsifiable concentrate | |
|---|---|
| Active ingredient | 10% |
| octylphenol polyethylene glycol ether (4–5 moles ethylene oxide) | 3% |
| calcium dodecylbenzensulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| A3. Dusts | a) | b) |
|---|---|---|
| Active ingredient | 5% | 8% |
| talcum | 95% | — |
| kaolin | — | 92% |

Ready for use dusts are obtained by mixing the active ingredient with the carriers and grinding the mixture in a suitable mill.

| A4. Extruder Granulate | |
|---|---|
| Active ingredient | 10% |
| sodium lignosulfonate | 2% |
| carboxymethylcellulose | 1% |
| kaolin | 87% |

The active ingredient or combination is mixed and ground with the adjuvants and the mixture is subsequently moistened with water. The mixture is extruded, granulated and the dried in a stream of air.

| A5. Coated Granule | |
| --- | --- |
| Active ingredient | 3% |
| polyethylene glycol (mol wt 200) | 3% |
| kaolin | 94% |

The active ingredient or combination is uniformly applied in a mixer to the kaolin moistened with polyethylene glycol. Non-dusty coated granulates are obtained in this manner.

| A6. Suspension Concentrate | |
| --- | --- |
| Active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous solution | 0.8% |
| water | 32% |

The active ingredient or combination is intimately mixed with the adjuvants giving a suspension concentrate from which suspensions of any desired concentration can be obtained by dilution with water.

What is claimed is:

1. A hybrid toxin comprising a monoclonal antibody or fragment thereof, which binds to insect brush border membranes, operably linked to a toxin moiety, wherein said antibody is produced by hybridoma cell line 2B5, 3B1, 10B6, 17F6, 14G1 or 16E4.

2. The hybrid toxin of claim 1 wherein said toxin moiety is selected from the group consisting of a Bacillus toxin, a Pseudomonas exotoxin, a phytolaccin, a gelonin, a ribonuclease, and a ribosome inactivating protein.

3. The hybrid toxin of claim 2 wherein said Bacillus toxin is a Bacillus endotoxin or a vegetative insecticidal protein.

4. The hybrid toxin of claim 3 wherein said Bacillus endotoxin is a Bt endotoxin.

5. A DNA sequence which encodes the hybrid toxin of claim 1.

6. An expression cassette comprising a promoter which directs expression in a plant operably linked to the DNA sequence of claim 5.

7. The expression cassette of claim 6 wherein said expression cassette further comprises a termination sequence operable in plants.

8. The DNA sequence of claim 5 wherein toxin moiety is selected from the group consisting of a Bacillus toxin, a Pseudomonas exotoxin, a phytolaccin, and a ribonuclease.

9. A plant cell comprising the DNA sequence of claim 5.

10. A plant cell comprising the expression cassette of claim 6.

11. A plant or the progeny thereof comprising the DNA sequence of claim 5.

12. A plant or the progeny thereof comprising the expression cassette of claim 6.

13. A plant or the progeny thereof expressing a hybrid toxin according to claim 1.

14. A plant according to claim 11 which is a maize plant.

15. A plant according to claim 11 which is a hybrid plant.

16. A fruit, tuber, grain or seed of the plant according to claim 11 treated with a protectant coating.

17. The fruit, tuber, grain or seed according to claim 16, wherein said protectant coating is selected from the group consisting of herbicides, insecticides, fungicides, bactericides, nematicides, molluscicides, and mixtures thereof.

18. A seed of the plant according to claim 11 treated with a protectant coating.

19. A recombinant microorganism comprising the DNA sequence of claim 5.

20. The recombinant microorganism of claim 19, wherein said recombinant microorganism is selected from the group consisting of Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, Alcaligenes, Saccharomyces, Cryptococcus, Kluyveromyces, Sporobolomyces, Rhodotorula, and Aureobasidium.

21. An entomocidal composition comprising the recombinant microorganism of claim 20 in an insecticidally-effective amount and a carrier.

22. An entomocidal composition comprising a hybrid toxin according to claim 1 in an insecticidally-effective amount and a carrier.

23. A fruit, tuber, grain, or seed of a plant, which is treated with the entomocidal composition according to claim 21.

24. A seed of a plant, which is treated with the entomocidal composition of claim 21.

25. A process for the stable transformation of a microbial or plant host comprising introducing a DNA sequence according to claim 5 into the genome of said host.

26. The process according to claim 25, wherein the host is a microbial host.

27. The process according to claim 25, wherein the host is a plant host.

* * * * *

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 357 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..357
      (D) OTHER INFORMATION: /note= "3B1 heavy chain variable
          region from pCIB4613"

(xi) SEQUENCE DESCRIPTION: SEQ ID NO:1:

```
CAG GTC AAA CTG CAG GAG TCT GGT GGA GGA TTG GTG CAG CCT AAA GGG      48
Gln Val Lys Leu Gln Glu Ser Gly Gly Gly Leu Val Gln Pro Lys Gly
 1               5                  10                  15

TCA TTG AAA CTC TCA TGT GCA GCC TCT GGA TTC ACC TTC AAT AAC TTC      96
Ser Leu Lys Leu Ser Cys Ala Ala Ser Gly Phe Thr Phe Asn Asn Phe
            20                  25                  30

GCC ATG AAC TGG GTC CGC CAG GCT CCA GGA AAG GGT TTG GAA TGG GTT     144
Ala Met Asn Trp Val Arg Gln Ala Pro Gly Lys Gly Leu Glu Trp Val
        35                  40                  45

GCT CGC ATA AGA AGT AAA AGT AAT AAT TAT GCA ACA TCT TAT GGC GAT     192
Ala Arg Ile Arg Ser Lys Ser Asn Asn Tyr Ala Thr Ser Tyr Gly Asp
    50                  55                  60

TCA GTG AAA GAC AGG TTC ACC GTC TCC AGA GAT GAT TCA CAA AGC ATG     240
Ser Val Lys Asp Arg Phe Thr Val Ser Arg Asp Asp Ser Gln Ser Met
65                  70                  75                  80

TTC TAT CTG CAA ATG AAC AAC TTG AAA ACT GAG GAC ACA GCC ATG TAT     288
Phe Tyr Leu Gln Met Asn Asn Leu Lys Thr Glu Asp Thr Ala Met Tyr
                85                  90                  95

TAC TGT GTG AGG GTA GTA TAC GGT GCT ATG GAC TAC TGG GGT CAA GGA     336
Tyr Cys Val Arg Val Val Tyr Gly Ala Met Asp Tyr Trp Gly Gln Gly
            100                 105                 110

ACC TCA GTC ACC GTC TCC TCA                                         357
Thr Ser Val Thr Val Ser Ser
        115
```

(2) INFORMATION FOR SEQ ID NO:2:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:2:

```
Gln Val Lys Leu Gln Glu Ser Gly Gly Gly Leu Val Gln Pro Lys Gly
 1               5                  10                  15

Ser Leu Lys Leu Ser Cys Ala Ala Ser Gly Phe Thr Phe Asn Asn Phe
             20                  25                  30

Ala Met Asn Trp Val Arg Gln Ala Pro Gly Lys Gly Leu Glu Trp Val
         35                  40                  45

Ala Arg Ile Arg Ser Lys Ser Asn Asn Tyr Ala Thr Ser Tyr Gly Asp
     50                  55                  60

Ser Val Lys Asp Arg Phe Thr Val Ser Arg Asp Asp Ser Gln Ser Met
 65                  70                  75                  80

Phe Tyr Leu Gln Met Asn Asn Leu Lys Thr Glu Asp Thr Ala Met Tyr
                 85                  90                  95

Tyr Cys Val Arg Val Val Tyr Gly Ala Met Asp Tyr Trp Gly Gln Gly
                100                 105                 110

Thr Ser Val Thr Val Ser Ser
            115
```

(2) INFORMATION FOR SEQ ID NO:3:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..333
        (D) OTHER INFORMATION: /note= "3B1 light chain variable
            region from pCIB4614 (#21Fv Ab)"

(xi) SEQUENCE DESCRIPTION: SEQ ID NO:3:

```
GAC ATT GTG CTG ACC CAG TCT CCA GCT TCT TTG GCT GTG TCT CTA GGG       48
Asp Ile Val Leu Thr Gln Ser Pro Ala Ser Leu Ala Val Ser Leu Gly
 1               5                  10                  15

CAG AGG GCC ACC ATC TCC TGC AGA GCC AGC GAA AGT GTT GAT CAT TAT       96
Gln Arg Ala Thr Ile Ser Cys Arg Ala Ser Glu Ser Val Asp His Tyr
             20                  25                  30

GAC ATT AGT TTT ATG AAC TGG TTC CAA CAG AAA CCA GGA CAG CCA CCC      144
Asp Ile Ser Phe Met Asn Trp Phe Gln Gln Lys Pro Gly Gln Pro Pro
         35                  40                  45

AAA CTC CTC ATC TAT GCT GCA TCC AAC CAA GGA TCC GGG GTC CCT GCC      192
Lys Leu Leu Ile Tyr Ala Ala Ser Asn Gln Gly Ser Gly Val Pro Ala
     50                  55                  60

AGG TTT AGT GGC AGT GGG TCT GGG ACA GAC TTC AGC CTC AAC ATC CAT      240
Arg Phe Ser Gly Ser Gly Ser Gly Thr Asp Phe Ser Leu Asn Ile His
 65                  70                  75                  80

CCT ATG GAG GAG GAT GAT ACT GCA ATA TAT TTC TGT CAG CAA AGT AGG      288
Pro Met Glu Glu Asp Asp Thr Ala Ile Tyr Phe Cys Gln Gln Ser Arg
                 85                  90                  95
```

```
GAA CTT CCG TAC ACG TTC GGA GGG GGG ACC ACG CTG GAA ATA AAA        333
Glu Leu Pro Tyr Thr Phe Gly Gly Gly Thr Thr Leu Glu Ile Lys
            100                 105                 110

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:4:

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp His Tyr
                20                  25                  30

Asp Ile Ser Phe Met Asn Trp Phe Gln Gln Lys Pro Gly Gln Pro Pro
            35                  40                  45

Lys Leu Leu Ile Tyr Ala Ala Ser Asn Gln Gly Ser Gly Val Pro Ala
     50                  55                  60

Arg Phe Ser Gly Ser Gly Ser Gly Thr Asp Phe Ser Leu Asn Ile His
 65              70                  75                  80

Pro Met Glu Glu Asp Asp Thr Ala Ile Tyr Phe Cys Gln Gln Ser Arg
                85                  90                  95

Glu Leu Pro Tyr Thr Phe Gly Gly Gly Thr Thr Leu Glu Ile Lys
            100                 105                 110

(2) INFORMATION FOR SEQ ID NO:5:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..372
        (D) OTHER INFORMATION: /note= "2B5 heavy chain variable
            region from pCIB4615"

(xi) SEQUENCE DESCRIPTION: SEQ ID NO:5:

CAG GTG CAA CTG CAG GAG TCT GGA GGA GGC TTG GTA CAG CCT GGG GGT         48
Gln Val Gln Leu Gln Glu Ser Gly Gly Gly Leu Val Gln Pro Gly Gly
 1               5                  10                  15

TCT CTG AGA CTC TCC TGT GCA ACT TCT GGG TTC ACC TTC ACT GAT TAC         96
Ser Leu Arg Leu Ser Cys Ala Thr Ser Gly Phe Thr Phe Thr Asp Tyr
                20                  25                  30

TAT ATG ACC TGG GTC CGC CAG CCT CCA GGA AAG GCA CTT GAG TGG TTG        144
Tyr Met Thr Trp Val Arg Gln Pro Pro Gly Lys Ala Leu Glu Trp Leu
            35                  40                  45

GGT TTT ATT AGA CAC AAA GCT AAT GGT TAC ACA ACA GAA TAC AGT GCA        192
Gly Phe Ile Arg His Lys Ala Asn Gly Tyr Thr Thr Glu Tyr Ser Ala
     50                  55                  60

TCT GTG AAG GGT CGG TTC ACC ATC TCC AGA GAT AAT TCC CAA AAC ATC        240
Ser Val Lys Gly Arg Phe Thr Ile Ser Arg Asp Asn Ser Gln Asn Ile
 65              70                  75                  80

CTC TAT CTT CAA ATG AAC ACC CTG AGA GCT GAG GAC AGT GCC ACT TAT        288
Leu Tyr Leu Gln Met Asn Thr Leu Arg Ala Glu Asp Ser Ala Thr Tyr
```

```
                   85                  90                  95
TAC TGT GCA AGA GAT ATA TGC TAT GGT TAC GAC GTT GGG GCT CTG GAC        336
Tyr Cys Ala Arg Asp Ile Cys Tyr Gly Tyr Asp Val Gly Ala Leu Asp
            100                 105                 110

TAC TGG GGT CAA GGA ACC TCA GTC ACC GTC TCC TCA                        372
Tyr Trp Gly Gln Gly Thr Ser Val Thr Val Ser Ser
        115                 120

(2) INFORMATION FOR SEQ ID NO:6:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:6:

Gln Val Gln Leu Gln Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Thr Trp Val Arg Gln Pro Pro Gly Lys Ala Leu Glu Trp Leu
        35                  40                  45

Gly Phe Ile Arg His Lys Ala Asn Gly Tyr Thr Thr Glu Tyr Ser Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Ile Cys Tyr Gly Tyr Asp Val Gly Ala Leu Asp
            100                 105                 110

Tyr Trp Gly Gln Gly Thr Ser Val Thr Val Ser Ser
        115                 120

(2) INFORMATION FOR SEQ ID NO:7:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..330
        (D) OTHER INFORMATION: /note= "2B5 light chain variable
            region from pCIB4616"

(xi) SEQUENCE DESCRIPTION: SEQ ID NO:7:

GAT ATC GTG ATG ACC CAG TCT CCT GCT TCC TTA GCT ATA TCT CTG GGG        48
Asp Ile Val Met Thr Gln Ser Pro Ala Ser Leu Ala Ile Ser Leu Gly
 1               5                  10                  15

CAG AGG GCC ACC ATC TCA TAC AGG GCC AGC AAA AGT GTC AGT ACA TCT        96
Gln Arg Ala Thr Ile Ser Tyr Arg Ala Ser Lys Ser Val Ser Thr Ser
            20                  25                  30

GGC TAT AGT TAT ATG CAC TGG AAC CAA CAG AAA CCA GGA CAG CCA CCC        144
Gly Tyr Ser Tyr Met His Trp Asn Gln Gln Lys Pro Gly Gln Pro Pro
        35                  40                  45

AGA CTC CTC ATC TAT CTT GTA TCC AAC CTA GAA TCT GGG GTC CCT GCC        192
Arg Leu Leu Ile Tyr Leu Val Ser Asn Leu Glu Ser Gly Val Pro Ala
```

```
                50                    55                      60
AGG  TTC  AGT  GGC  AGT  GGG  TCT  GGG  ACA  GAC  TTC  ACC  CTC  AAC  ATC  CAT      240
Arg  Phe  Ser  Gly  Ser  Gly  Ser  Gly  Thr  Asp  Phe  Thr  Leu  Asn  Ile  His
 65                      70                      75                      80

CCT  GTG  GAG  GAG  GAG  GAT  GCT  GCA  ACC  TAT  TAC  TGT  CAG  CAC  ATT  AGG      288
Pro  Val  Glu  Glu  Glu  Asp  Ala  Ala  Thr  Tyr  Tyr  Cys  Gln  His  Ile  Arg
                         85                      90                      95

GAG  CTT  ACA  CGT  TCG  GAG  GGG  GGA  CCA  AAG  CTG  GAA  ATA  AAA               330
Glu  Leu  Thr  Arg  Ser  Glu  Gly  Gly  Pro  Lys  Leu  Glu  Ile  Lys
              100                    105                     110
```

(2) INFORMATION FOR SEQ ID NO:8:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:8:

```
Asp  Ile  Val  Met  Thr  Gln  Ser  Pro  Ala  Ser  Leu  Ala  Ile  Ser  Leu  Gly
 1                    5                      10                     15

Gln  Arg  Ala  Thr  Ile  Ser  Tyr  Arg  Ala  Ser  Lys  Ser  Val  Ser  Thr  Ser
                   20                      25                     30

Gly  Tyr  Ser  Tyr  Met  His  Trp  Asn  Gln  Gln  Lys  Pro  Gly  Gln  Pro  Pro
              35                      40                     45

Arg  Leu  Leu  Ile  Tyr  Leu  Val  Ser  Asn  Leu  Glu  Ser  Gly  Val  Pro  Ala
         50                      55                     60

Arg  Phe  Ser  Gly  Ser  Gly  Ser  Gly  Thr  Asp  Phe  Thr  Leu  Asn  Ile  His
 65                      70                     75                      80

Pro  Val  Glu  Glu  Glu  Asp  Ala  Ala  Thr  Tyr  Tyr  Cys  Gln  His  Ile  Arg
                         85                     90                      95

Glu  Leu  Thr  Arg  Ser  Glu  Gly  Gly  Pro  Lys  Leu  Glu  Ile  Lys
              100                    105                    110
```

(2) INFORMATION FOR SEQ ID NO:9:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..165
        (D) OTHER INFORMATION: /note= "17F6 heavy chain variable
            region"

(xi) SEQUENCE DESCRIPTION: SEQ ID NO:9:

```
TCT  GTG  AAA  GGC  AGA  TTC  ACT  ATT  TCA  AGA  GAT  GAT  TCA  CAA  AGT  ACT      48
Ser  Val  Lys  Gly  Arg  Phe  Thr  Ile  Ser  Arg  Asp  Asp  Ser  Gln  Ser  Thr
 1                    5                      10                     15

GTC  TAC  CTG  GAG  ATG  AAC  ACG  CTA  AGA  GAG  GAA  GAC  ACT  GCC  ACT  TAT      96
Val  Tyr  Leu  Glu  Met  Asn  Thr  Leu  Arg  Glu  Glu  Asp  Thr  Ala  Thr  Tyr
                   20                      25                     30

TAT  TGT  TGT  AGA  GGG  GGG  GAG  GAG  GGG  TTT  CCT  TAC  TGG  GGG  CAA  GGG     144
Tyr  Cys  Cys  Arg  Gly  Gly  Glu  Glu  Gly  Phe  Pro  Tyr  Trp  Gly  Gln  Gly
              35                      40                     45

ACT  CTG  GTC  ACT  GTC  TCT  GCA                                                  165
```

```
Thr Leu Val Thr Val Ser Ala
    50              55
```

(2) INFORMATION FOR SEQ ID NO:10:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:10:

```
Ser Val Lys Gly Arg Phe Thr Ile Ser Arg Asp Asp Ser Gln Ser Thr
1               5                   10                  15

Val Tyr Leu Glu Met Asn Thr Leu Arg Glu Glu Asp Thr Ala Thr Tyr
            20                  25                  30

Tyr Cys Cys Arg Gly Gly Glu Glu Gly Phe Pro Tyr Trp Gly Gln Gly
        35                  40                  45

Thr Leu Val Thr Val Ser Ala
    50              55
```

(2) INFORMATION FOR SEQ ID NO:11:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..339
        (D) OTHER INFORMATION: /note= "17F6 light chain variable
            region"

(xi) SEQUENCE DESCRIPTION: SEQ ID NO:11:

```
GAC ATC GTG CTG ACC CAA TCT CCA TCC TCC CTG AGT GTG TCA GTA GGA        48
Asp Ile Val Leu Thr Gln Ser Pro Ser Ser Leu Ser Val Ser Val Gly
1               5                   10                  15

GAG AAG GTC ACC ATG AGC TGC AAG TCC AGT CAG AGT CTT TTC GAC AGT        96
Glu Lys Val Thr Met Ser Cys Lys Ser Ser Gln Ser Leu Phe Asp Ser
            20                  25                  30

GGA AAT CAA AAG AAC TCC TTG GCC TGG TAT CAG CAG AAA CCA GGG CAG       144
Gly Asn Gln Lys Asn Ser Leu Ala Trp Tyr Gln Gln Lys Pro Gly Gln
        35                  40                  45

CCT CCT AAA CTA TTG ATC TAC GGG ACA TCC ACT AGG GAT TCT GGG GTC       192
Pro Pro Lys Leu Leu Ile Tyr Gly Thr Ser Thr Arg Asp Ser Gly Val
    50                  55                  60

CCT GAT CGC TTC ACA GGC AGT GGA TCT GGG ACC GAT TTC ACT CTT ACC       240
Pro Asp Arg Phe Thr Gly Ser Gly Ser Gly Thr Asp Phe Thr Leu Thr
65                  70                  75                  80

ATC AGT GGT ATA CAG GCT GAA GAC CTG GCA GTT TAT TAC TGT CAG AAT       288
Ile Ser Gly Ile Gln Ala Glu Asp Leu Ala Val Tyr Tyr Cys Gln Asn
                85                  90                  95

GAT CAT TAT TAT CCG TTC ACG TTC GGA GGG GGG ACC AAG CTG GAG ATA       336
Asp His Tyr Tyr Pro Phe Thr Phe Gly Gly Gly Thr Lys Leu Glu Ile
                100                 105                 110

AAA                                                                    339
Lys
```

(2) INFORMATION FOR SEQ ID NO:12:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Ile Val Leu Thr Gln Ser Pro Ser Ser Leu Ser Val Ser Val Gly
 1               5                  10                  15

Glu Lys Val Thr Met Ser Cys Lys Ser Ser Gln Ser Leu Phe Asp Ser
            20                  25                  30

Gly Asn Gln Lys Asn Ser Leu Ala Trp Tyr Gln Gln Lys Pro Gly Gln
        35                  40                  45

Pro Pro Lys Leu Leu Ile Tyr Gly Thr Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Gly Ile Gln Ala Glu Asp Leu Ala Val Tyr Tyr Cys Gln Asn
                85                  90                  95

Asp His Tyr Tyr Pro Phe Thr Phe Gly Gly Gly Thr Lys Leu Glu Ile
            100                 105                 110

Lys
```

(2) INFORMATION FOR SEQ ID NO:13:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..357
        (D) OTHER INFORMATION: /note= "10B6 heavy chain variable
            region"

(xi) SEQUENCE DESCRIPTION: SEQ ID NO:13:

```
GAG GTG AAG GTG GAT GAG AGT GGG GGA GGC TTG GTA AGG CCT GGA AAT      48
Glu Val Lys Val Asp Glu Ser Gly Gly Gly Leu Val Arg Pro Gly Asn
 1               5                  10                  15

TCT CTG AAA CTC TCC TGT GAA ACC TCG GGA TTC ACT TTC AGT TAT TAT      96
Ser Leu Lys Leu Ser Cys Glu Thr Ser Gly Phe Thr Phe Ser Tyr Tyr
            20                  25                  30

TGG ATG CAC TGG CTT CGC CAG CCT CCA GGG AAG AGG CTG GAG TGG ATT     144
Trp Met His Trp Leu Arg Gln Pro Pro Gly Lys Arg Leu Glu Trp Ile
        35                  40                  45

GCT GTG ATT AAA GTC AAA TCT GCT AAT TAT GGA TCA AAT TAT GCA GAG     192
Ala Val Ile Lys Val Lys Ser Ala Asn Tyr Gly Ser Asn Tyr Ala Glu
    50                  55                  60

TCT GTG AAA GGC AGA TTC ACT ATT TCA AGA GAT GAT TCA AAT AGC GGT     240
Ser Val Lys Gly Arg Phe Thr Ile Ser Arg Asp Asp Ser Asn Ser Gly
65                  70                  75                  80

GTC TAC CTG CAG ATG AAC AGA TTA AGA GAA GAA GAC ACT GCC ACT TAT     288
Val Tyr Leu Gln Met Asn Arg Leu Arg Glu Glu Asp Thr Ala Thr Tyr
                85                  90                  95
```

```
TAT TGT AGT AGA GGG GGG GCC CCC GGG TTT CCT TAT TGG GGC CAA GGG        336
Tyr Cys Ser Arg Gly Gly Ala Pro Gly Phe Pro Tyr Trp Gly Gln Gly
            100                 105                 110

ACT CTG GTC ACT GTC TCT GCA                                            357
Thr Leu Val Thr Val Ser Ala
        115

(2) INFORMATION FOR SEQ ID NO:14:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:14:

Glu Val Lys Val Asp Glu Ser Gly Gly Gly Leu Val Arg Pro Gly Asn
  1               5                  10                  15

Ser Leu Lys Leu Ser Cys Glu Thr Ser Gly Phe Thr Phe Ser Tyr Tyr
             20                  25                  30

Trp Met His Trp Leu Arg Gln Pro Pro Gly Lys Arg Leu Glu Trp Ile
         35                  40                  45

Ala Val Ile Lys Val Lys Ser Ala Asn Tyr Gly Ser Asn Tyr Ala Glu
     50                  55                  60

Ser Val Lys Gly Arg Phe Thr Ile Ser Arg Asp Asp Ser Asn Ser Gly
 65                  70                  75                  80

Val Tyr Leu Gln Met Asn Arg Leu Arg Glu Glu Asp Thr Ala Thr Tyr
                 85                  90                  95

Tyr Cys Ser Arg Gly Gly Ala Pro Gly Phe Pro Tyr Trp Gly Gln Gly
            100                 105                 110

Thr Leu Val Thr Val Ser Ala
        115

(2) INFORMATION FOR SEQ ID NO:15:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..339
        (D) OTHER INFORMATION: /note= "10B6 light chain variable
            region"

(xi) SEQUENCE DESCRIPTION: SEQ ID NO:15:

GAT ATC GTG ATC ACC CAG TCT CCA TCC TCC CTA AGT GTG TCT TTA GGA         48
Asp Ile Val Ile Thr Gln Ser Pro Ser Ser Leu Ser Val Ser Leu Gly
  1               5                  10                  15

GAG AAG GTC ACT TTG AGC TGC AAG TCC AGT CAG AGT CTG TTT ACC GGT         96
Glu Lys Val Thr Leu Ser Cys Lys Ser Ser Gln Ser Leu Phe Thr Gly
             20                  25                  30

GGA GAT CAA AAG AAC TCC TTG GCC TGG TAC CAG CAG AAA GCA GGG CAG        144
Gly Asp Gln Lys Asn Ser Leu Ala Trp Tyr Gln Gln Lys Ala Gly Gln
         35                  40                  45

CCT CCT AGA CTG TTG ATC TAC GGG ACT TCC ACT AGG GAA TCT GGG GTC        192
Pro Pro Arg Leu Leu Ile Tyr Gly Thr Ser Thr Arg Glu Ser Gly Val
     50                  55                  60
```

```
CCT GAT CGC TTC ACA GGC AGT GGA TCT GGA ACC GAT TTC ACT CTT GCC       240
Pro Asp Arg Phe Thr Gly Ser Gly Ser Gly Thr Asp Phe Thr Leu Ala
65                  70                  75                  80

ATC AGC AGT GTG CAG GCT GAA GAC CTG GCA GGT TAT TAC TGT CAG AAT       288
Ile Ser Ser Val Gln Ala Glu Asp Leu Ala Gly Tyr Tyr Cys Gln Asn
                85                  90                  95

GAT CAT AGT TAT CCA TTC ACG TTC GGC TCG GGG ACA ATG TTG GAA GTA       336
Asp His Ser Tyr Pro Phe Thr Phe Gly Ser Gly Thr Met Leu Glu Val
            100                 105                 110

AAA                                                                   339
Lys (2) INFORMATION FOR SEQ ID NO:16:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:16:

Asp Ile Val Ile Thr Gln Ser Pro Ser Ser Leu Ser Val Ser Leu Gly
1               5                   10                  15

Glu Lys Val Thr Leu Ser Cys Lys Ser Ser Gln Ser Leu Phe Thr Gly
                20                  25                  30

Gly Asp Gln Lys Asn Ser Leu Ala Trp Tyr Gln Gln Lys Ala Gly Gln
            35                  40                  45

Pro Pro Arg Leu Leu Ile Tyr Gly Thr Ser Thr Arg Glu Ser Gly Val
        50                  55                  60

Pro Asp Arg Phe Thr Gly Ser Gly Ser Gly Thr Asp Phe Thr Leu Ala
65                  70                  75                  80

Ile Ser Ser Val Gln Ala Glu Asp Leu Ala Gly Tyr Tyr Cys Gln Asn
                85                  90                  95

Asp His Ser Tyr Pro Phe Thr Phe Gly Ser Gly Thr Met Leu Glu Val
            100                 105                 110

Lys (2) INFORMATION FOR SEQ ID NO:17:

(i) SEQUENCE CHARACTERISTICS:
        (A) LENGTH: 1797 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1797
        (D) OTHER INFORMATION: /note= "3B1 single chain antibody
            from pCIB4631"

(xi) SEQUENCE DESCRIPTION: SEQ ID NO:17:

ATG GGA TGG AGC TGG ATC TTT CTC TTC CTC CTG TCA GGA GCT GCA GGT        48
Met Gly Trp Ser Trp Ile Phe Leu Phe Leu Leu Ser Gly Ala Ala Gly
1               5                   10                  15

GTC CAT TGC CTA CTC GAG GAC ATT GTG CTG ACC CAG TCT CCA GCT TCT        96
Val His Cys Leu Leu Glu Asp Ile Val Leu Thr Gln Ser Pro Ala Ser
                20                  25                  30

TTG GCT GTG TCT CTA GGG CAG AGG GCC ACC ATC TCC TGC AGA GCC AGC       144
```

```
Leu Ala Val Ser Leu Gly Gln Arg Ala Thr Ile Ser Cys Arg Ala Ser
         35                  40                  45

GAA AGT GTT GAT CAT TAT GAC ATT AGT TTT ATG AAC TGG TTC CAA CAG        192
Glu Ser Val Asp His Tyr Asp Ile Ser Phe Met Asn Trp Phe Gln Gln
 50                  55                  60

AAA CCA GGA CAG CCA CCC AAA CTC CTC ATC TAT GCT GCA TCC AAC CAA        240
Lys Pro Gly Gln Pro Pro Lys Leu Leu Ile Tyr Ala Ala Ser Asn Gln
 65                  70                  75                  80

GGA TCC GGG GTC CCT GCC AGG TTT AGT GGC AGT GGG TCT GGG ACA GAC        288
Gly Ser Gly Val Pro Ala Arg Phe Ser Gly Ser Gly Ser Gly Thr Asp
                 85                  90                  95

TTC AGC CTC AAC ATC CAT CCT ATG GAG GAG GAT GAT ACT GCA ATA TAT        336
Phe Ser Leu Asn Ile His Pro Met Glu Glu Asp Asp Thr Ala Ile Tyr
                100                 105                 110

TTC TGT CAG CAA AGT AGG GAA CTT CCG TAC ACG TTC GGA GGG GGG ACC        384
Phe Cys Gln Gln Ser Arg Glu Leu Pro Tyr Thr Phe Gly Gly Gly Thr
            115                 120                 125

ACG CTG GAA ATA AAA CGG GCT GAT GCT GCA CCA ACT AGA TCT GGT GGC        432
Thr Leu Glu Ile Lys Arg Ala Asp Ala Ala Pro Thr Arg Ser Gly Gly
130                 135                 140

GGT GGC TCG GGC GGT GGT GGG TCG CTC GAG CAG GTC AAA CTG CAG GAG        480
Gly Gly Ser Gly Gly Gly Gly Ser Leu Glu Gln Val Lys Leu Gln Glu
145                 150                 155                 160

TCT GGT GGA GGA TTG GTG CAG CCT AAA GGG TCA TTG AAA CTC TCA TGT        528
Ser Gly Gly Gly Leu Val Gln Pro Lys Gly Ser Leu Lys Leu Ser Cys
                165                 170                 175

GCA GCC TCT GGA TTC ACC TTC AAT AAC TTC GCC ATG AAC TGG GTC CGC        576
Ala Ala Ser Gly Phe Thr Phe Asn Asn Phe Ala Met Asn Trp Val Arg
                180                 185                 190

CAG GCT CCA GGA AAG GGT TTG GAA TGG GTT GCT CGC ATA AGA AGT AAA        624
Gln Ala Pro Gly Lys Gly Leu Glu Trp Val Ala Arg Ile Arg Ser Lys
            195                 200                 205

AGT AAT AAT TAT GCA ACA TCT TAT GGC GAT TCA GTG AAA GAC AGG TTC        672
Ser Asn Asn Tyr Ala Thr Ser Tyr Gly Asp Ser Val Lys Asp Arg Phe
210                 215                 220

ACC GTC TCC AGA GAT GAT TCA CAA AGC ATG TTC TAT CTG CAA ATG AAC        720
Thr Val Ser Arg Asp Asp Ser Gln Ser Met Phe Tyr Leu Gln Met Asn
225                 230                 235                 240

AAC TTG AAA ACT GAG GAC ACA GCC ATG TAT TAC TGT GTG AGG GTA GTA        768
Asn Leu Lys Thr Glu Asp Thr Ala Met Tyr Tyr Cys Val Arg Val Val
                245                 250                 255

TAC GGT GCT ATG GAC TAC TGG GGT CAA GGA ACC TCA GTC ACC GTC TCC        816
Tyr Gly Ala Met Asp Tyr Trp Gly Gln Gly Thr Ser Val Thr Val Ser
                260                 265                 270

TCA GCC AAA ACG ACA CCC CCA TCT GTC TAT CCA CTG GCC CCT GGA TCT        864
Ser Ala Lys Thr Thr Pro Pro Ser Val Tyr Pro Leu Ala Pro Gly Ser
            275                 280                 285

AGA TCT GCT GCC CAA ACT AAC TCC ATG GTG ACC CTG GGA TGC CTG GTC        912
Arg Ser Ala Ala Gln Thr Asn Ser Met Val Thr Leu Gly Cys Leu Val
290                 295                 300

AAG GGC TAT TTC CCT GAG CCA GTG ACA GTG ACC TGG AAC TCT GGA TCC        960
Lys Gly Tyr Phe Pro Glu Pro Val Thr Val Thr Trp Asn Ser Gly Ser
305                 310                 315                 320

CTG TCC AGC GGT GTG CAC ACC TTC CCA GCT GTC CTG CAG TCT GAC CTC       1008
Leu Ser Ser Gly Val His Thr Phe Pro Ala Val Leu Gln Ser Asp Leu
                325                 330                 335

TAC ACT CTG AGC AGC TCA GTG ACT GTC CCC TCC AGC ACC TGG CCC AGC       1056
Tyr Thr Leu Ser Ser Ser Val Thr Val Pro Ser Ser Thr Trp Pro Ser
                340                 345                 350
```

```
GAG ACC GTC ACC TGC AAC GTT GCC CAC CCG GCC AGC AGC ACC AAG GTG        1104
Glu Thr Val Thr Cys Asn Val Ala His Pro Ala Ser Ser Thr Lys Val
        355                 360                 365

GAC AAG AAA ATT GTG CCC AGG GAT TGT GGT TGT AAG CCT TGC ATA TGT        1152
Asp Lys Lys Ile Val Pro Arg Asp Cys Gly Cys Lys Pro Cys Ile Cys
370                 375                 380

ACA GTC CCA GAA GTA TCA TCT GTC TTC ATC TTC CCC CCA AAG CCC AAG        1200
Thr Val Pro Glu Val Ser Ser Val Phe Ile Phe Pro Pro Lys Pro Lys
385                 390                 395                 400

GAT GTG CTC ACC ATT ACT CTG ACT CCT AAG GTC ACG TGT GTT GTG GTA        1248
Asp Val Leu Thr Ile Thr Leu Thr Pro Lys Val Thr Cys Val Val Val
                405                 410                 415

GAC ATC AGC AAG GAT GAT CCC GAG GTC CAG TTC AGC TGG TTT GTA GAT        1296
Asp Ile Ser Lys Asp Asp Pro Glu Val Gln Phe Ser Trp Phe Val Asp
            420                 425                 430

GAT GTG GAG GTG CAC ACA GCT CAG ACG CAA CCC CGG GAG GAG CAG TTC        1344
Asp Val Glu Val His Thr Ala Gln Thr Gln Pro Arg Glu Glu Gln Phe
        435                 440                 445

AAC AGC ACT TTC CGC TCA GTC AGT GAA CTT CCC ATC ATG CAC CAG GAC        1392
Asn Ser Thr Phe Arg Ser Val Ser Glu Leu Pro Ile Met His Gln Asp
450                 455                 460

TGG CTC AAT GGC AAG GAG TTC AAA TGC AGG GTC AAC AGT GCA GCT TTC        1440
Trp Leu Asn Gly Lys Glu Phe Lys Cys Arg Val Asn Ser Ala Ala Phe
465                 470                 475                 480

CCT GCC CCC ATC GAG AAA ACC ATC TCC AAA ACC AAA GGC AGA CCG AAG        1488
Pro Ala Pro Ile Glu Lys Thr Ile Ser Lys Thr Lys Gly Arg Pro Lys
                485                 490                 495

GCT CCA CAG GTG TAC ACC ATT CCA CCT CCC AAG GAG CAG ATG GCC AAG        1536
Ala Pro Gln Val Tyr Thr Ile Pro Pro Pro Lys Glu Gln Met Ala Lys
            500                 505                 510

GAT AAA GTC AGT CTG ACC TGC ATG ATA ACA GAC TTC TTC CCT GAA GAC        1584
Asp Lys Val Ser Leu Thr Cys Met Ile Thr Asp Phe Phe Pro Glu Asp
        515                 520                 525

ATT ACT GTG GAG TGG CAG TGG AAT GGG CAG CCA GCG GAG AAC TAC AAG        1632
Ile Thr Val Glu Trp Gln Trp Asn Gly Gln Pro Ala Glu Asn Tyr Lys
        530                 535                 540

AAC ACT CAG CCC ATC ATG AAC ACG AAT GGC TCT TAC TTC GTC TAC AGC        1680
Asn Thr Gln Pro Ile Met Asn Thr Asn Gly Ser Tyr Phe Val Tyr Ser
545                 550                 555                 560

AAG CTC AAT GTG CAG AAG AGC AAC TGG GAG GCA GGA AAT ACT TTC ACC        1728
Lys Leu Asn Val Gln Lys Ser Asn Trp Glu Ala Gly Asn Thr Phe Thr
                565                 570                 575

TGC TCT GTC TTA CAT GAG GGC CTG CAC AAC CAC CAT ACT GAG AAG AGC        1776
Cys Ser Val Leu His Glu Gly Leu His Asn His His Thr Glu Lys Ser
            580                 585                 590

CTC TCC CAC TCT CCT GGT AAA                                            1797
Leu Ser His Ser Pro Gly Lys
        595

(2) INFORMATION FOR SEQ ID NO:18:

(i) SEQUENCE CHARACTERISTICS:
        (A) LENGTH: 599 amino acids
        (B) TYPE: amino acid
        (D) TOPOLOGY: linear (ii) MOLECULE TYPE: protein (xi) SEQUENCE DESCRIPTION: SEQ ID NO:18:

Met Gly Trp Ser Trp Ile Phe Leu Phe Leu Leu Ser Gly Ala Ala Gly
 1               5                  10                  15
```

-continued

```
Val His Cys Leu Leu Glu Asp Ile Val Leu Thr Gln Ser Pro Ala Ser
             20                  25                  30

Leu Ala Val Ser Leu Gly Gln Arg Ala Thr Ile Ser Cys Arg Ala Ser
         35                  40                  45

Glu Ser Val Asp His Tyr Asp Ile Ser Phe Met Asn Trp Phe Gln Gln
     50                  55                  60

Lys Pro Gly Gln Pro Pro Lys Leu Leu Ile Tyr Ala Ala Ser Asn Gln
 65                  70                  75                  80

Gly Ser Gly Val Pro Ala Arg Phe Ser Gly Ser Gly Ser Gly Thr Asp
                 85                  90                  95

Phe Ser Leu Asn Ile His Pro Met Glu Glu Asp Thr Ala Ile Tyr
             100                 105                 110

Phe Cys Gln Gln Ser Arg Glu Leu Pro Tyr Thr Phe Gly Gly Gly Thr
            115                 120                 125

Thr Leu Glu Ile Lys Arg Ala Asp Ala Ala Pro Thr Arg Ser Gly Gly
        130                 135                 140

Gly Gly Ser Gly Gly Gly Gly Ser Leu Glu Gln Val Lys Leu Gln Glu
145                 150                 155                 160

Ser Gly Gly Gly Leu Val Gln Pro Lys Gly Ser Leu Lys Leu Ser Cys
                165                 170                 175

Ala Ala Ser Gly Phe Thr Phe Asn Asn Phe Ala Met Asn Trp Val Arg
            180                 185                 190

Gln Ala Pro Gly Lys Gly Leu Glu Trp Val Ala Arg Ile Arg Ser Lys
        195                 200                 205

Ser Asn Asn Tyr Ala Thr Ser Tyr Gly Asp Ser Val Lys Asp Arg Phe
    210                 215                 220

Thr Val Ser Arg Asp Asp Ser Gln Ser Met Phe Tyr Leu Gln Met Asn
225                 230                 235                 240

Asn Leu Lys Thr Glu Asp Thr Ala Met Tyr Tyr Cys Val Arg Val Val
                245                 250                 255

Tyr Gly Ala Met Asp Tyr Trp Gly Gln Gly Thr Ser Val Thr Val Ser
            260                 265                 270

Ser Ala Lys Thr Thr Pro Pro Ser Val Tyr Pro Leu Ala Pro Gly Ser
        275                 280                 285

Arg Ser Ala Ala Gln Thr Asn Ser Met Val Thr Leu Gly Cys Leu Val
    290                 295                 300

Lys Gly Tyr Phe Pro Glu Pro Val Thr Val Thr Trp Asn Ser Gly Ser
305                 310                 315                 320

Leu Ser Ser Gly Val His Thr Phe Pro Ala Val Leu Gln Ser Asp Leu
                325                 330                 335

Tyr Thr Leu Ser Ser Ser Val Thr Val Pro Ser Ser Thr Trp Pro Ser
            340                 345                 350

Glu Thr Val Thr Cys Asn Val Ala His Pro Ala Ser Ser Thr Lys Val
        355                 360                 365

Asp Lys Lys Ile Val Pro Arg Asp Cys Gly Cys Lys Pro Cys Ile Cys
    370                 375                 380

Thr Val Pro Glu Val Ser Ser Val Phe Ile Phe Pro Pro Lys Pro Lys
385                 390                 395                 400

Asp Val Leu Thr Ile Thr Leu Thr Pro Lys Val Thr Cys Val Val Val
                405                 410                 415

Asp Ile Ser Lys Asp Asp Pro Glu Val Gln Phe Ser Trp Phe Val Asp
            420                 425                 430

Asp Val Glu Val His Thr Ala Gln Thr Gln Pro Arg Glu Glu Gln Phe
```

```
                435              440                445
Asn Ser Thr Phe Arg Ser Val Ser Glu Leu Pro Ile Met His Gln Asp
    450                 455                460

Trp Leu Asn Gly Lys Glu Phe Lys Cys Arg Val Asn Ser Ala Ala Phe
465                 470                475                 480

Pro Ala Pro Ile Glu Lys Thr Ile Ser Lys Thr Lys Gly Arg Pro Lys
                485                 490                495

Ala Pro Gln Val Tyr Thr Ile Pro Pro Lys Glu Gln Met Ala Lys
                500                 505                510

Asp Lys Val Ser Leu Thr Cys Met Ile Thr Asp Phe Phe Pro Glu Asp
                515                 520                525

Ile Thr Val Glu Trp Gln Trp Asn Gly Gln Pro Ala Glu Asn Tyr Lys
        530                 535                540

Asn Thr Gln Pro Ile Met Asn Thr Asn Gly Ser Tyr Phe Val Tyr Ser
545                 550                 555                560

Lys Leu Asn Val Gln Lys Ser Asn Trp Glu Ala Gly Asn Thr Phe Thr
                565                 570                575

Cys Ser Val Leu His Glu Gly Leu His Asn His Thr Glu Lys Ser
                580                 585                590

Leu Ser His Ser Pro Gly Lys
        595
```

(2) INFORMATION FOR SEQ ID NO:19:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: other nucleic acid
        (A) DESCRIPTION: oligonucleotide KE109A28 used to make
           101bp Sty I/Bgl II fragment for pCIB4612

(xi) SEQUENCE DESCRIPTION: SEQ ID NO:19:

CAAGGACGAG TATGAACGAC ATAACAGCTA TACCTGTGAG GCCACTCACA AGACATCAAC    60

TTCACCCATT GTCAAGAGCT TCAACAGGAA TGAGTGTTAG G    101

(2) INFORMATION FOR SEQ ID NO:20:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: other nucleic acid
        (A) DESCRIPTION: oligonucleotide KE110A28 used to make
           101bp Sty I/Bgl II fragment for pCIB4612

(xi) SEQUENCE DESCRIPTION: SEQ ID NO:20:

GATCCCTAAC ACTCATTCCT GTTGAAGCTC TTGACAATGG GTGAAGTTGA TGTCTTGTGA    60

GTGGCCTCAC AGGTATAGCT GTTATGTCGT TCATACTCGT C    101

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
            (A) DESCRIPTION: oligonucleotide KE111A28 used to make
                71bp Xho I/Dde I fragment for pCIB4612

(xi) SEQUENCE DESCRIPTION: SEQ ID NO:21:

TCGAGGGTAC CGAGCTCTAG ATCTGTATCC ATCTTCCCAC CATCCAGTGA GCAGTTAACA          60

TCTGGAGGTG CC                                                             72

(2) INFORMATION FOR SEQ ID NO:22:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: other nucleic acid
            (A) DESCRIPTION: oligonucleotide KE112A28 used to make
                71bp Xho I/Dde I fragment for pCIB4612

(xi) SEQUENCE DESCRIPTION: SEQ ID NO:22:

TGAGGCACCT CCAGATGTTA ACTGCTCACT GGATGGTGGG AAGATGGATA CAGATCTAGA          60

GCTCGGTACC C                                                              71

(2) INFORMATION FOR SEQ ID NO:23:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: oligonucleotide KE106A28 used to make
                40bp Xho I/Nco I fragment for pCIB4611

(xi) SEQUENCE DESCRIPTION: SEQ ID NO:23:

TCGAGGGTAC CGAGCTCTAG ATCTGCTGCC CAAACTAACT C                             41

(2) INFORMATION FOR SEQ ID NO:24:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: oligonucleotide KE107A28 used to make
                40bp Xho I/Nco I fragment for pCIB4611

(xi) SEQUENCE DESCRIPTION: SEQ ID NO:24:

CATGGAGTTA GTTTGGGCAG CAGATCTAGA GCTCGGTACC C                             41

(2) INFORMATION FOR SEQ ID NO:25:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: oligonucleotide KE108A28 used to make
                40bp Bst XI/Bam HI fragment for pCIB4611

(xi) SEQUENCE DESCRIPTION: SEQ ID NO:25:

CTGGTAAAGG CGGCCGCATC GATTAAGTCG ACCCGCGGG                                39

(2) INFORMATION FOR SEQ ID NO:26:

(i) SEQUENCE CHARACTERISTICS:
       (A) LENGTH: 47 base pairs
       (B) TYPE: nucleic acid
       (C) STRANDEDNESS: single
       (D) TOPOLOGY: linear (ii) MOLECULE TYPE: other nucleic acid
       (A) DESCRIPTION:  oligonucleotide KE105A28 used to make
           40bp Bst XI/Bam HI fragment for pCIB4611

(xi) SEQUENCE DESCRIPTION: SEQ ID NO:26:

GATCCCCGCG GGTCGACTTA ATCGATGCGG CCGCCTTTAC CAGGAGA          47

(2) INFORMATION FOR SEQ ID NO:27:

(i) SEQUENCE CHARACTERISTICS:
       (A) LENGTH: 7 base pairs
       (B) TYPE: nucleic acid
       (C) STRANDEDNESS: single
       (D) TOPOLOGY: linear (ii) MOLECULE TYPE: other nucleic acid
       (A) DESCRIPTION:  plant consensus translational initiation
           sequence for pCIB4610

(xi) SEQUENCE DESCRIPTION: SEQ ID NO:27:

AACAATG                                                      7

(2) INFORMATION FOR SEQ ID NO:28:

(i) SEQUENCE CHARACTERISTICS:
       (A) LENGTH: 7 base pairs
       (B) TYPE: nucleic acid
       (C) STRANDEDNESS: single
       (D) TOPOLOGY: linear (ii) MOLECULE TYPE: other nucleic acid
       (A) DESCRIPTION:  plant consensus translational initiation
           sequence for pCIB4600

(xi) SEQUENCE DESCRIPTION: SEQ ID NO:28:

TCCGATG                                                      7

(2) INFORMATION FOR SEQ ID NO:29:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION:  PCR primer KE102A28 used to generate 83bp
           fragment for pCIB4610

(xi) SEQUENCE DESCRIPTION: SEQ ID NO:29:

CGAAGTTAAC AGATCTAGAG CTCGG                                  25

(2) INFORMATION FOR SEQ ID NO:30:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: other nucleic acid (A) DESCRIPTION: PCR primer KE101A28 used to generate 83bp
        fragment for pCIB4610

(xi) SEQUENCE DESCRIPTION: SEQ ID NO:30:

CGGGATCCAA CAATGGGATG GAGCTGGATC TT                              32

(2) INFORMATION FOR SEQ ID NO:31:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: other nucleic acid
        (A) DESCRIPTION: oligonucleotide encoding an endoplasmic
            reticulum signal peptide from Kabat et al., 1987

(xi) SEQUENCE DESCRIPTION: SEQ ID NO:31:

GATCCAACAA TGGGATGGAG CTGGATCTTT CTCTTCCTCC TGTCAGTTGT TACCCTACCT    60

CGACCTAGAA AGAGAAGGAG GACAGTGGAG CTGCAGGTGT CCATTGCCTA CTCGAGGGTA   120

CCGAGCTCCT CGACGTCCAC AGGTAACGGA TGAGCTCCGA TGGC                    164

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (v) FRAGMENT TYPE: internal (ix) FEATURE:
        (A) NAME/KEY: Domain
        (B) LOCATION: 1..10
        (D) OTHER INFORMATION: /note= "10 amino acid domain linker
            between light and heavy Fv fragments"

(xi) SEQUENCE DESCRIPTION: SEQ ID NO:32:

Gly Gly Gly Gly Ser Gly Gly Gly Gly Ser
1               5                   10

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: oligonucleotide KE147A28 used to make 36bp
            linker for pCIB4631

(xi) SEQUENCE DESCRIPTION: SEQ ID NO:33:

GATCTGGTGG CGGTGGCTCG GGCGGTGGTG GGTCGC                             36

(2) INFORMATION FOR SEQ ID NO:34:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid

```
            (A) DESCRIPTION:  oligonucleotide KE182A28 used to make 36bp
                linker for pCIB4631

(xi) SEQUENCE DESCRIPTION: SEQ ID NO:34:

TCGAGCGACC CACCACCGCC CGAGCCACCG CCACCA                                36

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  PCR primer NC200 used to generate 700bp
            fragment containing the 3B1 single chain antibody coding
            sequence for fusion to PE40

(xi) SEQUENCE DESCRIPTION: SEQ ID NO:35:

CGAAGCTTGA CATTGTGCTG ACCCAG                                           26

(2) INFORMATION FOR SEQ ID NO:36:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  PCR primer NC202 used to generate 700bp
            fragment containing the 3B1 single chain antibody coding
            sequence for fusion to PE40

(xi) SEQUENCE DESCRIPTION: SEQ ID NO:36:

GCCCTCTAGA AGCATGCCTG AGGAGACGGT GACTGA                                36

(2) INFORMATION FOR SEQ ID NO:37:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  PCR primer NC92 used to amplify antibody
            genes (xi) SEQUENCE DESCRIPTION: SEQ ID NO:37:

GTCTCGAGGA YATYSWGMTS ACCCARTCT                                        29

(2) INFORMATION FOR SEQ ID NO:38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  PCR primer NC130 used to amplify antibody
            genes (xi) SEQUENCE DESCRIPTION: SEQ ID NO:38:

GCAGATCTAG TTGGTGCAGC ATCAGCCCG                                        29

(2) INFORMATION FOR SEQ ID NO:39:
```

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: PCR primer NC91 used to amplify antibody
            genes (xi) SEQUENCE DESCRIPTION: SEQ ID NO:39:

GTCTCGAGCA GGTSMARCTG CAGSAGTCWG                                    30

(2) INFORMATION FOR SEQ ID NO:40:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: PCR primer NC114 used to amplify antibody
            genes (xi) SEQUENCE DESCRIPTION: SEQ ID NO:40:

GCAGATCTAG ATCCAGGGGC CAGTGGATA                                     29

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: PCR primer NC111 used to amplify antibody
            genes (xi) SEQUENCE DESCRIPTION: SEQ ID NO:41:

GCAGATCTGC AGGAGACGAG GGGGAAGACA TT                                 32

(2) INFORMATION FOR SEQ ID NO:42:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: PCR primer NC117 used to amplify antibody
            genes (xi) SEQUENCE DESCRIPTION: SEQ ID NO:42:

GCAGATCTGC AGCCAGGGAC CAAGGGATA                                     29

(2) INFORMATION FOR SEQ ID NO:43:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (ix) FEATURE:
            (A) NAME/KEY: Domain
            (B) LOCATION: 1..22
            (D) OTHER INFORMATION: /note= "alternative domain linker
                between light and heavy Fv fragments"

(xi) SEQUENCE DESCRIPTION: SEQ ID NO:43:

Gly Pro Gly Pro Ser Thr Pro Pro Thr Pro Ser Pro Ser Thr Pro Pro
1               5                  10                  15

Thr Pro Ser Gly Pro Gly
            20

(2) INFORMATION FOR SEQ ID NO:44:

(i) SEQUENCE CHARACTERISTICS:
            (A) LENGTH: 357 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: CDS
            (B) LOCATION: 1..357
            (D) OTHER INFORMATION: /note= "14G1 heavy chain variable
                region from pCIB4635"

(xi) SEQUENCE DESCRIPTION: SEQ ID NO:44:

GAG GTG AAG CTT GTG GAG TCT GGG GGA GGC TTG GTG AGG CCT GGA AAT        48
Glu Val Lys Leu Val Glu Ser Gly Gly Gly Leu Val Arg Pro Gly Asn
1               5                  10                  15

TCT CTG AAA CTC TCC TGT GTT ACC TCG GGA TTC ACT TTC AGT AAC TAC        96
Ser Leu Lys Leu Ser Cys Val Thr Ser Gly Phe Thr Phe Ser Asn Tyr
            20                  25                  30

CGG ATG CAC TGG CTT CGC CAG CCT CCA GGG AAG AGG CTG GAG TGG ATT       144
Arg Met His Trp Leu Arg Gln Pro Pro Gly Lys Arg Leu Glu Trp Ile
35                  40                  45

GCT GTA ATT ACA CTC AAA TCT GAT AAT TAT GGA ACA ATT TAT GCA GAA       192
Ala Val Ile Thr Leu Lys Ser Asp Asn Tyr Gly Thr Ile Tyr Ala Glu
    50                  55                  60

TCT GTG AAA GGC AGA TTC ACC ATT TCA AGA GAA GAT TCA GAA AGC AGC       240
Ser Val Lys Gly Arg Phe Thr Ile Ser Arg Glu Asp Ser Glu Ser Ser
65                  70                  75                  80

ATC TAC CTG CAG ATG AAC AGA TTA AGA GAG GAA GAC ACT GCC ACT TAT       288
Ile Tyr Leu Gln Met Asn Arg Leu Arg Glu Glu Asp Thr Ala Thr Tyr
            85                  90                  95

TAC TGT AGT AGA GGT AGT GAC TGG GGA TTT CCT TAT TGG GGG CAA GGG       336
Tyr Cys Ser Arg Gly Ser Asp Trp Gly Phe Pro Tyr Trp Gly Gln Gly
        100                 105                 110

ACT CTG GTC ACT GTC TCT GCA                                           357
Thr Leu Val Thr Val Ser Ala
115

(2) INFORMATION FOR SEQ ID NO:45:

(i) SEQUENCE CHARACTERISTICS:
            (A) LENGTH: 119 amino acids
            (B) TYPE: amino acid
            (D) TOPOLOGY: linear (ii) MOLECULE TYPE: protein (xi) SEQUENCE DESCRIPTION: SEQ ID NO:45:

```
Glu Val Lys Leu Val Glu Ser Gly Gly Leu Val Arg Pro Gly Asn
 1               5                  10                  15

Ser Leu Lys Leu Ser Cys Val Thr Ser Gly Phe Thr Phe Ser Asn Tyr
                20                  25                  30

Arg Met His Trp Leu Arg Gln Pro Pro Gly Lys Arg Leu Glu Trp Ile
            35                  40                  45

Ala Val Ile Thr Leu Lys Ser Asp Asn Tyr Thr Ile Tyr Ala Glu
    50                  55                  60

Ser Val Lys Gly Arg Phe Thr Ile Ser Arg Glu Asp Ser Glu Ser Ser
 65                 70                  75                  80

Ile Tyr Leu Gln Met Asn Arg Leu Arg Glu Glu Asp Thr Ala Thr Tyr
                85                  90                  95

Tyr Cys Ser Arg Gly Ser Asp Trp Gly Phe Pro Tyr Trp Gly Gln Gly
            100                 105                 110

Thr Leu Val Thr Val Ser Ala
        115
```

(2) INFORMATION FOR SEQ ID NO:46:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..339
        (D) OTHER INFORMATION: /note= "14G1 light chain variable
            region from pCIB4636"

(xi) SEQUENCE DESCRIPTION: SEQ ID NO:46:

```
GAT ATT GTG ATG ACC CAG TCT CCA TCC TCC CTG AGT GTG TCA GCA GGA      48
Asp Ile Val Met Thr Gln Ser Pro Ser Ser Leu Ser Val Ser Ala Gly
 1               5                  10                  15

GAG AAG GTC ACT ATG AAC TGC AAG TCC AGT CAG AGT CTG TTA AAT AGT      96
Glu Lys Val Thr Met Asn Cys Lys Ser Ser Gln Ser Leu Leu Asn Ser
                20                  25                  30

GGA AAT CAA AAG CAC TAC TTG GCC TGG TAC CAG CAG AAA CCA GGC CAG     144
Gly Asn Gln Lys His Tyr Leu Ala Trp Tyr Gln Gln Lys Pro Gly Gln
            35                  40                  45

CCT CCT AAA CTG TTG ATC TAC GGG GCA TCC ACT AGG GAA TCT GGG GTC     192
Pro Pro Lys Leu Leu Ile Tyr Gly Ala Ser Thr Arg Glu Ser Gly Val
    50                  55                  60

CCT GAT CGC TTC ACA GGC AGT GGG TCT GGA ACC GAT TTC ACT CTT ACC     240
Pro Asp Arg Phe Thr Gly Ser Gly Ser Gly Thr Asp Phe Thr Leu Thr
 65                 70                  75                  80

ATC AGC AGT GTG CAG GCT GAA GAC CTG GCA GTT TAT TTC TGT CAG AAT     288
Ile Ser Ser Val Gln Ala Glu Asp Leu Ala Val Tyr Phe Cys Gln Asn
                85                  90                  95

GAT CGT AGT TAT CCG TTC ACA TTC GCC TCG GGG ACA AAG TTG GAA ATA     336
Asp Arg Ser Tyr Pro Phe Thr Phe Ala Ser Gly Thr Lys Leu Glu Ile
            100                 105                 110
```

```
      AAA                                                                  339
      Lys (2) INFORMATION FOR SEQ ID NO:47:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:47:

Asp Ile Val Met Thr Gln Ser Pro Ser Ser Leu Ser Val Ser Ala Gly
 1               5                  10                  15

Glu Lys Val Thr Met Asn Cys Lys Ser Ser Gln Ser Leu Leu Asn Ser
             20                  25                  30

Gly Asn Gln Lys His Tyr Leu Ala Trp Tyr Gln Gln Lys Pro Gly Gln
         35                  40                  45

Pro Pro Lys Leu Leu Ile Tyr Gly Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Phe Cys Gln Asn
                 85                  90                  95

Asp Arg Ser Tyr Pro Phe Thr Phe Ala Ser Gly Thr Lys Leu Glu Ile
            100                 105                 110

Lys (2) INFORMATION FOR SEQ ID NO:48:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: PCR primer DB91 used to amplify antibody
            genes (iii) HYPOTHETICAL: NO (iv) ANTI-SENSE: NO (xi) SEQUENCE DESCRIPTION: SEQ ID NO:48:

ACGTCTCGAG GARGTGAAGC TKRWKGARWC TG                                         32

(2) INFORMATION FOR SEQ ID NO:49:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: PCR primer DB114 used to amplify antibody
            genes (iii) HYPOTHETICAL: NO (iv) ANTI-SENSE: NO (xi) SEQUENCE DESCRIPTION: SEQ ID NO:49:
```

| | |
|---|---|
| -continued | |
| CAATTCGCAT ATGAGATCCA GGGGCCAGTG GATA | 34 |